US012774496B2

(12) United States Patent
Mulé et al.

(10) Patent No.: US 12,774,496 B2
(45) **Date of Patent: *Oct. 27, 2026**

(54) IMMUNE GENE SIGNATURES IN CANCER

(71) Applicant: H. Lee Moffitt Cancer Center and Research Institute, Inc., Tampa, FL (US)

(72) Inventors: James J. Mulé, Odessa, FL (US); Domenico Coppola, Tampa, FL (US); Timothy J. Yeatman, Thonotosassa, FL (US); Andrey Loboda, Philadelphia, PA (US); Michael V. Nebozhyn, Yeadon, PA (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/330,177

(22) Filed: May 25, 2021

(65) Prior Publication Data

US 2021/0381061 A1 Dec. 9, 2021

Related U.S. Application Data

(63) Continuation of application No. 16/868,293, filed on May 6, 2020, now abandoned, which is a continuation of application No. 16/029,499, filed on Jul. 6, 2018, now Pat. No. 10,648,040, which is a continuation of application No. 15/171,713, filed on Jun. 2, 2016, now Pat. No. 10,041,129, which is a continuation of application No. 13/575,354, filed as application No. PCT/US2011/022845 on Jan. 28, 2011, now Pat. No. 9,404,926.

(60) Provisional application No. 61/299,798, filed on Jan. 29, 2010.

(51) Int. Cl.

| | |
|---|---|
| ***C12Q 1/6886*** | (2018.01) |
| ***G01N 33/575*** | (2026.01) |
| ***G01N 33/57515*** | (2026.01) |

(52) U.S. Cl.

CPC ......... *C12Q 1/6886* (2013.01); *G01N 33/575* (2026.01); *G01N 33/57515* (2026.01); *G01N 33/57557* (2026.01); *C12Q 2600/106* (2013.01); *C12Q 2600/118* (2013.01); *C12Q 2600/158* (2013.01)

(58) Field of Classification Search

None

See application file for complete search history.

(56) References Cited

U.S. PATENT DOCUMENTS

| | | | | |
|---|---|---|---|---|
| 5,595,756 A * | 1/1997 | Bally | A61K 9/1272 264/4.1 |
| 9,404,926 B2 * | 8/2016 | Mulé | G01N 33/57415 |
| 10,041,129 B2 * | 8/2018 | Mulé | C12Q 1/6886 |
| 10,583,183 B2 * | 3/2020 | Magliocco | C12Q 1/6886 |
| 10,648,040 B2 * | 5/2020 | Mulé | C12Q 1/6886 |
| 2006/0275844 A1 | 12/2006 | Linke et al. | |
| 2007/0218512 A1 | 9/2007 | Strongin et al. | |
| 2009/0215053 A1 | 8/2009 | Galon et al. | |
| 2009/0258795 A1 | 10/2009 | Cowens et al. | |
| 2015/0292030 A1 | 10/2015 | McConkey et al. | |
| 2017/0175199 A1 | 6/2017 | Magliocco et al. | |
| 2018/0080087 A1 | 3/2018 | Bacus | |
| 2018/0216197 A1 | 8/2018 | Davicioni et al. | |
| 2023/0323468 A1 | 10/2023 | Li et al. | |

FOREIGN PATENT DOCUMENTS

| | | | |
|---|---|---|---|
| WO | WO-2007045996 A1 * | 4/2007 | C12Q 1/6886 |
| WO | WO 2009/114547 | 9/2009 | |
| WO | WO 2011/094483 | 8/2011 | |
| WO | WO 2015/157623 | 10/2015 | |
| WO | WO 2022/047209 | 3/2022 | |

OTHER PUBLICATIONS

Venet et al (PLoS Comput Biol. Oct. 2011;7(10):e1002240) (Year: 2011).*

Ahmadzada et al (J Clin Med. Jun. 15, 2018;7(6):153) (Year: 2018).*

McKean et al (Am Soc Clin Oncol Educ Book. May 2020;40:e275-e291) (Year: 2020).*

Christiansen et al (Mol Cancer Ther, 2004, 3:1493-1501) (Year: 2004).*

Topp et al (Journal of Controlled Release, 1998, 53:15-23) (Year: 1998).*

Sporn et al, "Chemoprevention of Cancer," Carcinogenesis, vol. 21 (2000), 525-530 (Year: 2000).*

Gura T (Science, 1997, 278(5340): 1041-1042 (Year: 1997).*

Jain RK (Scientific American, Jul. 1994,58-65) (Year: 1994).*

Brooks (Genome Res. 2012. 22: 183-187) (Year: 2012).*

Ahmadzada et al., "An update on predictive biomarkers for treatment selection in non-small cell lung cancer," Journal of Clinical Medicine, Jun. 2018, 7(6):153, 12 pages.

Alexandrescu et al., "Immunotherapy for melanoma: current status and perspectives," J Immunother, 2010, 33(6):570-90.

Aspord et al., "Breast cancer instructs dendritic cells to prime interleukin 13-secreting CD4+ T cells that facilitate tumor development," J Exp Med, 2007, 204:1037-1047.

Auerbach et al., "Angiogenesis Assays: Problems and Pitfalls," Cancer and Metastasis Reviews, 2000 19: 167-172.

Bell et al., "In breast carcinoma tissue, immature dendritic cells reside within the tumor, whereas mature dendritic cells are located in peritumoral areas," J Exp Med, 1999, 190:1417-1426.

(Continued)

*Primary Examiner* — Brian Gangle
*Assistant Examiner* — Andrea K Mccollum
(74) *Attorney, Agent, or Firm* — Fish & Richardson P.C.

(57) ABSTRACT

This invention relates to methods for selecting a treatment, treating, and predicting survival time in subjects with cancer, such as colorectal cancer, based on tumor expression levels of chemokines, cytotoxic genes, and/or dendritic cell genes.

10 Claims, 11 Drawing Sheets

(56) References Cited

OTHER PUBLICATIONS

Bogunovic et al., "Immune profile and mitotic index of metastatic melanoma lesions enhance clinical staging in predicting patient survival," PNAS, 2009, 106:20429-20434.
Brooks, "Translational genomics: The challenge of developing cancer biomarkers," Genome Res, 2012, 22: 183-187.
Carragher et al., "Ectopic lymphoid tissues and local immunity," Semin Immunol, 2008, 20:26-42 (author manuscript).
Chaves et al., "Immunohistochemical detection of mismatch repair gene proteins as a useful tool for the identification of colorectal carcinoma with the mutator phenotype," J Pathol, 2000, 191:355-360.
Chiba et al., "Intraepithelial CD8+ T-cell-count becomes a prognostic factor after a longer follow up period in human colorectal carcinoma: possible association with suppression of micrometastasis," Br J Cancer, 2004, 91:1711-1717.
Christiansen et al., "Biological impediments to monoclonal antibody-based cancer immunotherapy," Molecular Cancer Therapeutics, Nov. 1, 2004, 3(11):1493-501.
Coppola and Mule, "Ectopic lymph nodes within human solid tumors," J Clin Oncol, 2008, 26:4369-4370.
Coppola et al., "Unique ectopic lymph node-like structures present in human primary colorectal carcinoma are identified by immune gene array profiling," Am. J. Pathol, 2011, 179(1):37-45.
Coronella et al., "Antigen-driven oligoclonal expansion of tumor-infiltrating B cells in infiltrating ductal carcinoma of the breast," J Immunol, 2002, 169:1829-1836.
Coronella-Wood and Hersh, "Naturally occurring B-cell responses to breast Cancer," Review. Cancer Immunol Immunother, 2003, 52:715-738.
Curiel et al., "Specific recruitment of regulatory T cells in ovarian carcinoma fosters immune privilege and predicts reduced survival," Nat Med, 2004, 10:942-949.
Dieu-Nosjean et al., "Long-term survival for patients with non-small-cell lung cancer with intratumoral lymphoid structures," J Clin Oncol, 2008, 26:4410-4417.
Dubinett et al., "Chemokines: Can Effector Cells be Re-directed to the Site of Tumor?" Cancer J., 2010, 16(4):325-335 (author manuscript).
Eggermont et al., "Anti-CTLA-4 antibody adjuvant therapy in melanoma," Semin Oncol, 2010, 37(5):455-9.
Eisenthal et al., "Expression of dendritic cells in ovarian tumors correlates with clinical outcome in patients with ovarian cancer," Hum Pathol, 2001, 32:803-807.
Galon et al., "Type, density, and location of immune cells within human colorectal tumors predict clinical outcome," Science, 2006, 313:1960-1964.
Ganesan and Bakhshi, "Systemic therapy for melanoma," Natl Med J India, 2010, 23(1):21-7.
GeurtsvanKessel et al., "Dendritic cells are crucial for maintenance of tertiary lymphoid structures in the lung of influenza virus-infected mice," J Exp Med, 2009, 206:2339-2349.
Golovina and Vonderheide, "Regulatory T cells: overcoming suppression of T-cell immunity," Cancer J, 2010, 16(4):342-7.
Gura, "Systems for Identifying New Drugs Are Often Faulty," Science, 1997, 278(5340): 1041-1042.
Harlin et al., "Chemokine expression in melanoma metastases associated with CD8+ T-cell recruitment," Cancer Res, 2009, 69:3077-3085.
Hoelzinger et al., "Blockade of CCL 1 inhibits T regulatory cell suppressive function enhancing tumor immunity without affecting T effector responses," J Immunol, 2010, 184:6833-6842.
International Preliminary Report on Patentability in International Application No. PCT/US2011/022845, dated Aug. 9, 2012, 7 pages.
International Search Report and Written Opinion in International Application No. PCT/US2011/022845, dated Oct. 27, 2011, 11 pages.
Jain, "Barriers to drug delivery in solid tumors," Scientific American, Jul. 1, 1994, 271(1):58-65.
Jemal et al., "Cancer Statistics," CA Cancer J Clin, 2008, 58:71-96.
Kakar et al., "Muscinous carcinoma of the colon: correlation of loss of mismatch repair enzymes with clinicopathologis features and survival," Modern Pathol, 2004, 17:696-700.
Kim et al., "CD4+CD3- accessory cells costimulate primed CD4 T cells through OX40 and CD30 at sites where T cells collaborate with B cells," Immunity 2003, 18:643-654.
Kirk et al., "The dynamics of the T-cell antitumor response: Chemokine-secreting dendritic cells can prime tumor-reactive T cells extranodally," Cancer Res, 2001, 61:794-8802.
Klinke II, "A multiscale systems perspective on cancer, immunotherapy, and Interleukin-12," Mol Cancer, 2010, 9:242.
Kruger et al., "Immune based therapies in cancer," Histol Histopathol., 2007, 22(6):687-96.
Kurabayashi et al., "Distribution of tumor-infiltrating dendritic cells in human non-small cell lung carcinoma in relation to apoptosis," Pathol Int, 2004, 54:302-310.
Luscieti et al., "Human lymph node morphology as a function of age and site," J Clin Pathol, 1980, 33:454-461.
Manzo et al., "Systematic microanatomical analysis ofCXCL13 and CCL21 in situ production and progressive lymphoid organization in rheumatoid synovitis," Eur J Immunol, 2005, 35:1347-1359.
Marinkovic et al., "Interaction of mature CD3+CD4+ T cells with dendritic cells triggers the development of tertiary lymphoid structures in the thyroid," J Clin Invest, 2006, 116:2622-2632.
Mazzolini et al., "Immunotherapy and immunoescape in colorectal cancer," World J. Gastroenterol, 2007, 13(44):5822-5831.
McKean et al., "Biomarkers in precision cancer immunotherapy: promise and challenges," American Society of Clinical Oncology Educational Book, May 1, 2020, 40:e275-91.
Messina et al., "12-Chemokine Gene Signature Identifies Lymph Node-like Structures in Melanoma: Potential for Patient Selection for Immunotherapy?," Scientific Reports, 2012, 2:765.
Michael-Robinson et al., "Tumour infiltrating lymphocytes and apoptosis are independent features in colorectal cancer stratified according to microsatellite instability status," Gut, 2001, 48:360-366.
Mira et al., "Statins induce regulatory T cell recruitment via a CCLI dependent pathway," J Immunol, 2008, 181:3524-3534.
Moschella et al., "Combinations strategies for enhancing the efficacy of immunotherapy in cancer patients," Ann NY Acad Sci, 2010, 1194:169-78.
Nagorsen et al., "Natural T-cell response against MHC class I epitopes of epithelial cell adhesion molecule, her-2/neu, and carcinoembryonic antigen in patients with colorectal cancer," Cancer Res, 2000. 60:4850-4854.
Nagorsen et al., "Tumor-infiltrating macrophages and dendritic cells in buman colorectal cancer; Relation to local regulatory T cells, systemic T-cell response against tumor-associated antigens and survival," J Transl Med, 2007, 5:62.
Olszewski, "De novo lymph node formation in chronic inflammation of the human leg," Ann NY Acad Sci, 2002, 979:166-177.
Prabhakaran et al., "Evaluation of invasive breast cancer samples using a 12-chemokine gene expression score: correlation with clinical outcomes," Breast Cancer Research, 2017, 19: 71.
Ropponen et al., "Prognostic value of tumour-infiltrating lymphocytes (TILs) in colorectal Cancer," J Pathol, 1997, 182:318-324.
Singh et al., "Lymphoid neogenesis and immune infiltration in aged liver," Hepatology, 2008, 47:1680-1690 (author manuscript).
Sporn et al., "Chemoprevention of Cancer," Carcinogenesis, 2000, 21: 525-530.
Timmer et al., "Inflammation and ectopic lymphoid structures in rheumatoid arthritis synovial tissues dissected by genomics technology: Identification of the interleukin-7 signaling pathway in tissues with lymphoid neogenesis," Arthritis Rheum, 2007, 56:2492-2502.
Topp et al., "Antibody transport in cultured tumor cell layers," Journal of Controlled Release, Apr. 30, 1998. 53(1-3):15-23.
Tougeron et al., "Tumor-infiltrating lymphocytes in colorectal cancers with microsatellite instability are correlated with the number and spectrum of frameshift mutations," Modern Pathol, 2009, 22:1186-1195.

(56) References Cited

OTHER PUBLICATIONS

Toulza et al., "Human T-lymphotropic virus type I-induced CC chemokine ligand 22 maintains a high frequency of functional FoxP3+ regulatory T cells," J Immunol, 2010, 185:183-189.
Tsunoda et al., "Differential expression ofCa(2+)-binding proteins on follicular dendritic cells in non-neoplastic and neoplastic lymphoid follicles," Am J Pathol, 1999, 155:805-814.
Ulloa-Montoya et al., "Predictive Gene Signature in MAGE-A3 Antigen-Specific Cancer Immunotherapy," Journal of Clinical Oncology, Published ahead of print on May 28, 2013 at http://jco.ascopubs.org/cgi/doi/10.1200/JCO,2012.44.3762.
Van de Pavert et al., "Chemokine CXCL13 is essential for lymph node initiation and is induced by retinoic acid and neuronal stimulation," Nat Immunol, 2009, 10:1193-1199.
Venet et al., "Most Random Gene Expression Signatures Are Significantly Associated with Breast Cancer Outcome," PLoS Comput Biol, 2011, 7(10):e1002240.
Wang et al., "Prediction of Response to Anticancer Immunotherapy Using Gene Signatures," Journal of Clinical Oncology, Published ahead of print on May 28, 2013 at http://jco.ascopubs.org/cgi/doi/10.1200/JCO.2013.49.2157.
Xu et al., "Identification of carly intestinal neoplasia protein bio markers using laser capture microdissection and MALDI MS," Molecular and Cellular Proteomics, 2009, 8(5):936-945.
Yamazaki et al., "CCR6 regulates the migration of inflammatory and regulatory T cells," J Immunol, 2008, 181:8391-8401.
Yeatman et al., "On the eve of personalized medicine in oncology," Cancer Res, 2008, 68:7250-7252.
Zeid and Muller, "S100 positive dendritic cells in human lung tumors associated with cell differentiation and enhanced survival," Pathology, 1993, 25:338-343.
Aran et al., "xCell: digitally portraying the tissue cellular heterogeneity landscape," Genome Biology, Nov. 2017, vol. 18, 14 pages.
Cabrita et al., "Tertiary lymphoid structures improve immunotherapy and survival in melanoma," Nature, Jan. 2020, 577(7791):561, 20 pages.
Cochrane Library, Advanced Bladder Cancer Overview Collaboration, "Neoadjuvant chemotherapy for invasive bladder cancer," Cochrane Database Syst Rev, Apr. 2005, 2:CD005246, 27 pages.
Del Bene et al., "Neoadjuvant vs. Adjuvant chemotherapy in muscle invasive bladder cancer (MIBC): Analysis from the RISC database," Front Oncol., Nov. 2018, vol. 8, Article 463, 9 pages.
Fenstermacher et al., "Implementing personalized medicine in a Cancer Center," The Cancer Journal, Nov. 2011, 17(6):528-536.
Helmink et al., "B cells and tertiary lymphoid structures promote immunotherapy response," Nature, Jan. 2020, 577(7791):549-555.
Kroeger et al., "Tumor-infiltrating plasma cells are associated with tertiary lymphoid structures, cytolytic T-cell responses, and superior prognosis in ovarian cancer," Clinical Cancer Research, Jun. 15, 2016; 22(12):3005-3015.
Li et al., "The 12-CK score: Global measurement of tertiary lymphoid Structure," Frontiers in Immunology, Jun. 2021, vol. 12, 10 pages.
Liu et al., "An Integrated TCGA Pan-Cancer Clinical Data Resource to Drive High-Quality Survival Outcome Analytics," Cell, Apr. 2018, 173(2):400-416.
Mariathasan et al., "TGFβ attenuates tumour response to PD-L1 blockade by contributing to exclusion of T cells, " Nature, Feb. 2018, 554(7693):544-548.
Necchi et al., "Impact of molecular subtyping and immune infiltration on pathological response and outcome following neoadjuvant pembrolizumab in muscle-invasive bladder cancer," European Urology, Jun. 2020, 77(6):701-710.
Necchi et al., "Pembrolizumab as neoadjuvant therapy before radical cystectomy in patients with muscle-invasive urothelial bladder carcinoma (PURE-01): An open-label, single-arm, phase II study," Journal of Clinical Oncology, Dec. 2018, 36(34):3353-3360.
Necchi et al., "Updated results of PURE-01 with preliminary activity of neoadjuvant pembrolizumab in patients with muscle-invasive bladder carcinoma with variant histologies," European Urology, Apr. 2020, 77(4):439-446 (Abstract Only).
PCT International Preliminary Report on Patentability in International Application No. PCT/US2021/048028, mailed on Mar. 9, 2023, 6 pages.
PCT International Search Report and Written Opinion in International Application No. PCT/US2021/048028, mailed on Jan. 6, 2022, 7 pages.
Petitprez et al., "B cells are associated with survival and immunotherapy response in sarcoma," Nature, Jan. 2020, 577(7791):556-560.
Rosenberg et al., "Atezolizumab in patients with locally advanced and metastatic urothelial carcinoma who have progressed following treatment with platinum-based chemotherapy: a single-arm, multicentre, phase 2 trial," Lancet, May 2016, 387(10031):1909-1920.
Sautes-Fridman et al., "Tertiary lymphoid structures in the era of cancer immunotherapy," Nature Reviews Cancer, Jun. 2019, 19(6):307-325.
Sharma et al., "CD8 tumor-infiltrating lymphocytes are predictive of survival in muscle-invasive urothelial carcinoma," Proc Natl Acad Sci USA, Mar. 2007, 104(10):3967-3972.
Van Dijk et al., "The cancer immunogram as a framework for personalized immunotherapy in urothelial cancer," European Urology, Mar. 2019, 75(3):435-444.
Wang et al., "EMT- and stroma-related gene expression and resistance to PD-1 blockade in urothelial cancer," Nature Communications, Aug. 2018, 9(1):3503, 12 pages.
Yin et al., "Neoadjuvant chemotherapy for muscle-invasive bladder cancer: A systematic review and two-step meta-analysis," The Oncologist, Jun. 2016, 21(6):708-715.
Pfannstiel et al., "The tumor immune microenvironment drives a prognostic relevance that correlates with bladder cancer subtypes," Cancer Immunology Research, Jun. 2019, 7(6):923-38.

* cited by examiner

FIG. 2A
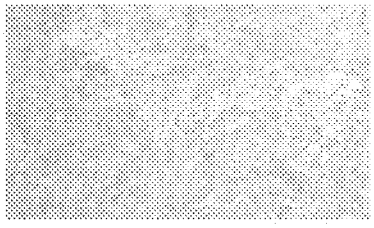
FIG. 2B
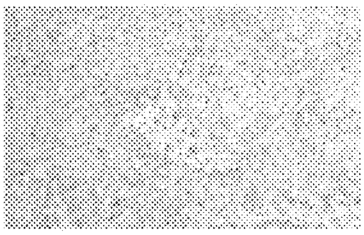
FIG. 2C
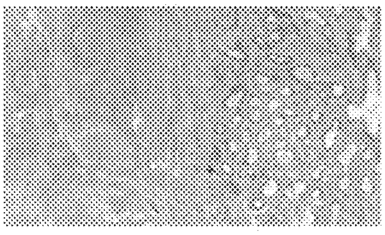
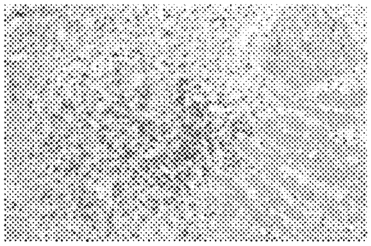
FIG. 2D
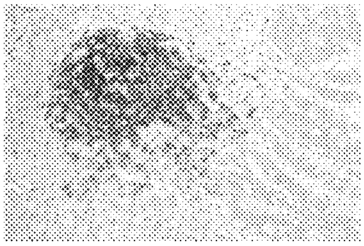
FIG. 2E
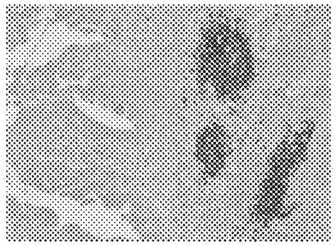
FIG. 2F
FIG. 2G
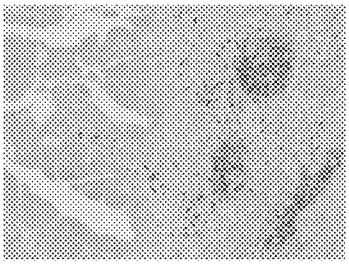
FIG. 2H
FIG. 2I
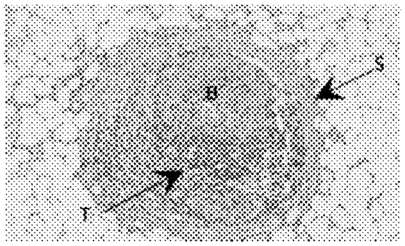
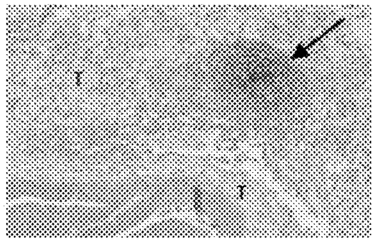
FIG. 2J Dendritic Genes (Confusion Matrix: TP=10, FP=3, FN=0, TN=8)

plotted value=input value - adjustment, adjustment=-0.062887

Cytotoxic Genes (Confusion Matrix: TP=9, FP=1, FN=4, TN=7)

IMMUNE GENE SIGNATURES IN CANCER

CLAIM OF PRIORITY

This application is a continuation of U.S. application Ser. No. 16/029,499, filed on Jul. 6, 2018, which is a continuation of U.S. application Ser. No. 15/171,713, filed on Jun. 2, 2016, now U.S. Pat. No. 10,041,129, which is a continuation of U.S. application Ser. No. 13/575,354, filed on Jul. 26, 2012, now U.S. Pat. No. 9,404,926, which is a U.S. National Phase Application of International Patent Application No. PCT/US2011/022845, filed on Jan. 28, 2011, which claims the benefit of U.S. Patent Application No. 61/299,798, filed on Jan. 29, 2010. The entire contents of the foregoing are hereby incorporated by reference.

FEDERALLY SPONSORED RESEARCH OR DEVELOPMENT

This invention was made with Government support under Grant No. R01 CA148995-01 awarded by the National Institutes of Health. The Government has certain rights in the invention.

TECHNICAL FIELD

This invention relates to methods for identifying tumors associated with immune cell infiltration, and for making a prognosis in subjects with cancer, such as colorectal cancer.

BACKGROUND

Tumor-induced, host immune response has been described in breast (2-5), lung (6, 7), ovarian (8, 9), and colorectal adenocarcinoma (CRC) (10, 11) among other solid tumor types. This response may include fibrosis, lymphocytic or neutrophilic infiltration, and other reactive changes within the tumor and/or in the surrounding tissue.

SUMMARY

The present invention is based, at least in part, on the discovery of gene signatures that predict the presence of infiltrating immune cells. Expression levels of these genes can be used to optimize or select treatment and predict survival in subjects with tumors.

Thus, in a first aspect, the invention provides methods for predicting survival time for a subject who has a tumor. The methods include obtaining cells from the tumor; determining one or more of:

(i) gene expression levels of chemokines chemokine (C-C motif) ligand 2 (CCL2), CCL3, CCL4, CCL5, CCL8, chemokine (C-C motif) ligand 18 (pulmonary and activation-regulated) (CCL18), CCL19, CCL21, chemokine (C-X-C motif) ligand 9 (CXCL9), CXCL10, CXCL11, and CXCL13 in the tumor cells;

(ii) gene expression levels of cytotoxic cell genes cathepsin H (CTSH), CTSC, CTSD, CTSE, CTSO, CTSS, CTSZ, granzyme A (GZMA), GZMB, GZMH, GZMK, Fcgamma receptor (FcgammaR) type IIa (FCGR2A), FCGR2B, FCGR2C, Fcgamma receptor (FcgammaR) type IIIa (FCGR3A), FCGR3B in the tumor cells; or (iii) gene expression levels of dendritic cell genes S100P Binding Protein (S100PBP), S100 calcium-binding protein A10 (S100A10), S100A6, S100A7L1, S100G, S100A1, S100A7, S100A14, S100A16, S100A2, S100A11, S100P, S100Z, S100A3, S100A13, S100A12, S100B, S100A4, S100A9, S100A8, and CD209 antigen (CD209) in the tumor cells;

comparing the tumor gene expression levels to reference gene expression levels; and predicting longer survival time if tumor gene expression levels are above the reference gene expression levels, or predicting shorter survival time if tumor gene expression levels are below the reference gene expression levels.

In another aspect, the invention provides methods for monitoring an immunotherapy in a subject who has a tumor. The methods include obtaining cells from the tumor; determining first gene expression levels of one or more of:

(i) gene expression levels of chemokines CCL2, CCL3, CCL4, CCL5, CCL8, CCL18, CCL19, CCL21, CXCL9, CXCL10, CXCL11, and CXCL13 in the tumor cells;

(ii) gene expression levels of cytotoxic cell genes cathepsin H (CTSH), CTSC, CTSD, CTSE, CTSO, CTSS, CTSZ, granzyme A (GZMA), GZMB, GZMH, GZMK, Fcgamma receptor (FcgammaR) type IIa (FCGR2A), FCGR2B, FCGR2C, Fcgamma receptor (FcgammaR) type IIIa (FCGR3A), FCGR3B in the tumor cells; or (iii) gene expression levels of dendritic cell genes S100PBP, S100A10, S100A6, S100A7L1, S100G, S100A1, S100A7, S100A14, S100A16, S100A2, S100A11, S100P, S100Z, S100A3, S100A13, S100A12, S100B, S100A4, S100A9, S100A8, and CD209 in the tumor cells;

administering one or more doses of an immunotherapy to the subject; determining second gene expression levels of the same genes in the tumor cells; and comparing the first and second gene expression levels, wherein second gene expression levels that are higher than the first gene expression levels indicate that the treatment is effective, and second gene expression levels that are the same as or lower that the first gene expression levels indicate that the treatment is not effective.

In another aspect, the invention provides methods for treating a subject who has a tumor. The methods include obtaining cells from the tumor; determining expression levels of one or more of:

(i) gene expression levels of chemokines CCL2, CCL3, CCL4, CCL5, CCL8, CCL18, CCL19, CCL21, CXCL9, CXCL10, CXCL11, and CXCL13 in the tumor cells;

(ii) gene expression levels of cytotoxic cell genes cathepsin H (CTSH), CTSC, CTSD, CTSE, CTSO, CTSS, CTSZ, granzyme A (GZMA), GZMB, GZMH, GZMK, Fcgamma receptor (FcgammaR) type IIa (FCGR2A), FCGR2B, FCGR2C, Fcgamma receptor (FcgammaR) type IIIa (FCGR3A), FCGR3B in the tumor cells; or (iii) gene expression levels of dendritic cell genes S100PBP, S100A10, S100A6, S100A7L1, S100G, S100A1, S100A7, S100A14, S100A16, S100A2, S100A11, S100P, S100Z, S100A3, S100A13, S100A12, S100B, S100A4, S100A9, S100A8, and CD209 in the tumor cells;

comparing the tumor gene expression levels to reference gene expression levels; and selecting for the subject a treatment comprising an immunotherapy if tumor gene expression levels are above the reference gene expression levels, or selecting for the subject a treatment not comprising an immunotherapy if tumor gene expression levels are below the reference gene expression levels.

In a further aspect, the invention provides methods for selecting a treatment for a subject who has a tumor. The methods include obtaining cells from the tumor; determining one or more of:

(i) gene expression levels of chemokines CCL2, CCL3, CCL4, CCL5, CCL8, CCL18, CCL19, CCL21, CXCL9, CXCL10, CXCL11, and CXCL13 in the tumor cells;

(ii) gene expression levels of cytotoxic cell genes cathepsin H (CTSH), CTSC, CTSD, CTSE, CTSO, CTSS, CTSZ, granzyme A (GZMA), GZMB, GZMH, GZMK, Fcgamma receptor (FcgammaR) type IIa (FCGR2A), FCGR2B, FCGR2C, Fcgamma receptor (FcgammaR) type IIIa (FCGR3A), FCGR3B in the tumor cells; and (iii) gene expression levels of dendritic cell genes S100PBP, S100A10, S100A6, S100A7L1, S100G, S100A1, S100A7, S100A14, S100A16, S100A2, S100A11, S100P, S100Z, S100A3, S100A13, S100A12, S100B, S100A4, S100A9, S100A8, and CD209 in the tumor cells;

comparing the tumor gene expression levels to reference gene expression levels; and selecting for the subject a treatment comprising an immunotherapy if tumor gene expression levels are above the reference gene expression levels, or selecting for the subject a treatment not comprising an immunotherapy if tumor gene expression levels are below the reference gene expression levels.

In some embodiments of the methods described herein, determining gene expression levels comprises determining protein levels. In some embodiments of the methods described herein, determining gene expression levels comprises determining mRNA levels.

In some embodiments of the methods described herein, the methods include determining chemokine gene expression levels. In some embodiments of the methods described herein, the methods include determining cytotoxic cell gene expression levels. In some embodiments of the methods described herein, the methods include determining dendritic cell gene expression levels. In some embodiments of the methods described herein, the methods include determining chemokine gene expression levels and cytotoxic cell gene expression levels. In some embodiments of the methods described herein, the methods include determining cytotoxic cell gene expression levels and dendritic cell gene expression levels. In some embodiments of the methods described herein, the methods include determining chemokine gene expression levels and dendritic cell gene expression levels. In some embodiments of the methods described herein, the methods include determining chemokine gene expression levels, cytotoxic cell gene expression levels, and dendritic cell gene expression levels.

In some embodiments of the methods described herein, the longer survival time is 2 years or more, and the shorter survival time is less than 2 years.

In some embodiments of the methods described herein, the methods further include communicating predicted survival time to the subject or a health care provider. In some embodiments of the methods described herein, the methods further include communicating information regarding the effectiveness of a treatment to the subject or a health care provider. In some embodiments of the methods described herein, the methods further include communicating information regarding treatment or selection of a treatment to the subject or a health care provider.

In some embodiments of the methods described herein, immunotherapy comprises administering to the subject dendritic cells or peptides with adjuvant, a DNA-based vaccine, cytokines, cyclophosphamide, anti-interleukin-2R immunotoxin, or an anti-cancer antibody. In some embodiments, the antibody is anti-CD137, anti-programmed death-1 receptor (PD1), or anti-cytotoxic T-lymphocyte antigen-4 (CTLA-4). In some embodiments, the immunotherapy comprises administering to the subject tumor-pulsed dendritic cells.

In some embodiments of the methods described herein, the subject is a human.

In some embodiments of the methods described herein, the tumor is a solid tumor.

In some embodiments of the methods described herein, the tumor is colorectal cancer.

A "subject" as described herein can be any subject having a proliferative disorder. For example, the subject can be any mammal, such as a human, including a human cancer patient. Exemplary nonhuman mammals include a nonhuman primate (such as a monkey or ape), mouse, rat, goat, cattle, pig, horse, sheep, cat, and dog.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2A-J are a set of images showing the results of H & E staining and immunohistochemistry analysis of primary CRCs. All 10 of the lowest gene signature-scored CRCs revealed a lightly dispersed or absent lymphocytic peritumoral host response, and low to no appreciable expression of B cell (i.e., CD20; 2A) and T cell (i.e., CD3; 2B) markers. All 11 of the highest gene signature-scored CRCs, revealed a marked peritumoral lymphocytic host response organized as ectopic lymph node-like structures by hematoxylin and eosin staining (arrows; 2C) and by immunohistochemistry (2D-I). $CD20^{+}$ (2E, F) and $CD79a^{+}$ (2G) B cells and $CD21^{+}$ follicular dendritic cells (J) are concentrated in the center of follicles with CD3+(2D, H, I) T cells appearing in the parafollicular cortex or marginal zones, with some dispersion into the follicles. In some cases, a fibrous stroma was observed to encapsulate a follicle (2I). In panels H and I, T=T cells, B=B cells, and S=stroma. In panel J, T=tumor; the follicle (arrow) is at the front edge of the invading colonic adenocarcinoma.

FIG. 3A is a heatmap showing mean-centered intensities (averaged within each probe set across all tumors shown). FIG. 3B is a bar graph displaying chemokine score: the mean value of chemokines as averaged across all probe sets shown in 3A.

FIG. 5A is a heatmap showing mean-centered intensities (averaged within each probe set across all tumors shown). FIG. 5B is a bar plot displaying the mean value of cytotoxic genes as averaged across all probe sets.

FIG. 6A is a heatmap showing mean-centered intensities (averaged within each probe set across all tumors shown). FIG. 6B is a bar plot displaying the mean value of dendritic cell marker genes as averaged across all probe sets.

DETAILED DESCRIPTION

Figure 1A:
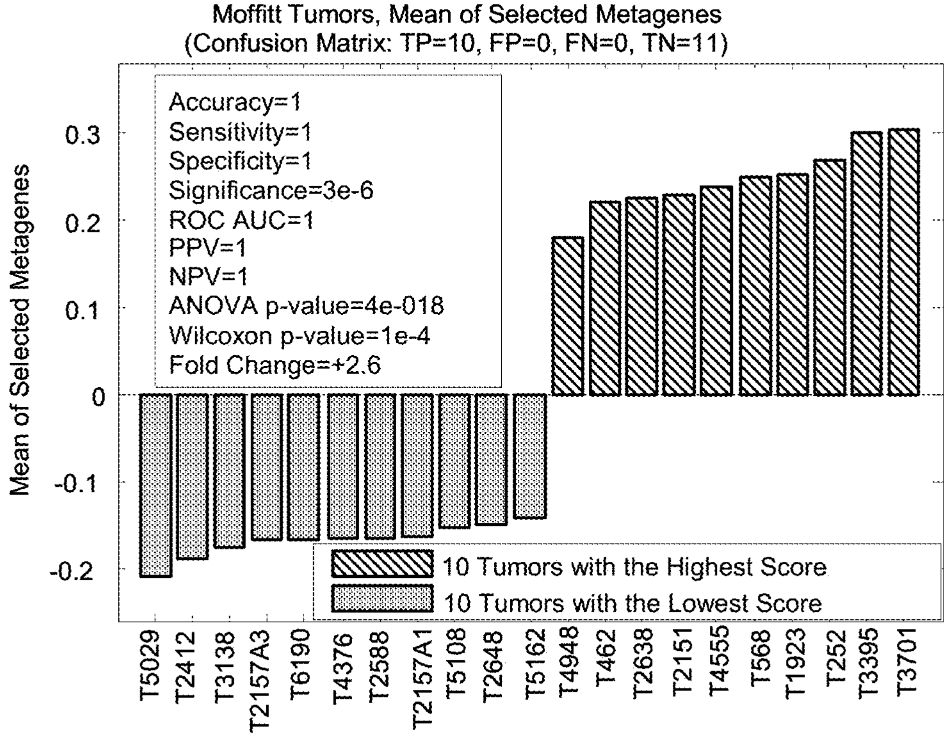
FIG. 1A is a bar graph illustrating the observed range of the immune response as represented by the metagene #1 score. The barplot shows CRCs that have 11 highest and 10 lowest values of the mean score of selected immune metagenes grouped by whether they had the highest 11 or lowest 10 scores and sorted by the mean metagene score.

It has been shown that some growing, human solid tumors are infiltrated by immune cells. Data characterizing the nature of this host immune response in a wide variety of distinct tumor types have been published in the recent literature (2-9), including primary CRCs (14). As shown herein, profiling gene signatures predicts the presence of infiltrating immune cells, and expression levels of these genes can be used to assign a prognosis and select or optimize treatment in subjects with tumors.

Methods of Assigning a Prognosis or Predicting Survival

The methods can be used to monitor a treatment (e.g., an immunotherapy), or to select a treatment, e.g., to select a treatment regime including an immunotherapy for a subject. In addition, the methods described herein can be used for, e.g., to assist in, assigning a prognosis or predicting survival in a subject who has a tumor, e.g., a solid tumor.

As used herein, the term "cancer" refers to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. In general, a cancer will be associated with the presence of one or more tumors, i.e., abnormal cell masses. The term "tumor" is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. In general, the methods described herein can be practiced on subjects with solid tumors.

Tumors include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, cancers evaluated by the methods described herein include those that are particularly immunogenic, e.g., neuroblastoma, melanoma, and renal cell cancer.

In some embodiments, cancers evaluated by the methods described herein include epithelial cancers, such as a lung cancer (e.g., non-small-cell lung cancer (NSCLC)), breast cancer, colorectal cancer, head and neck cancer, or ovarian cancer. Epithelial malignancies are cancers that affect epithelial tissues.

Lymphoid Structures in Solid Tumors

Lymphoid structures have been described in solid tumors. As examples, Coronella-Wood et al. (2, 3) have described breast tumor-infiltrating lymphocytes composed of B cell aggregates containing interdigitating CD21+ follicular dendritic cells. The presence of ectopic, organized lymphoid tissue has also been reported in ovarian (8, 9, 19); colon (20, 21); and lung tumors (6, 7), which has mostly focused on the presence of dendritic cell subpopulations, the level of which predicted better prognosis in some tumor types (7, 8, 22). A similar correlation was recently reported for patients with CRC (10).

Colorectal Adenocarcinoma (CRC)

In some embodiments, the methods herein can be used to select treatment or predict survival in a subject who has colorectal adenocarcinoma (CRC). CRC is one of the most common malignancies, accounting for approximately 15% of all cancer-related deaths in the U.S. The prevalence of CRC increases with age, the largest number of tumors occurring during the sixth decade. The expected annual incidence of this tumor has risen over the last decade and 149,000 new cases were estimated in 2009 (1). If not diagnosed and treated early, this tumor spreads through the entire bowel wall, extends to adjacent organs, and eventually metastasizes to regional lymph nodes and distant sites. The majority of deaths from CRC occur in patients with metastatic late stage tumors, which are incurable most of the time.

CRC is known to elicit an inflammatory immune reaction composed of acute and/or chronic inflammatory cells, including lymphocytes, infiltrating the tumor as well as the surrounding colonic wall. The lymphocytic component of this response has been shown to include some antigen-specific T cells originating without prior immunotherapy (12, 13). As described herein, immune gene-related signatures predict the presence of unique histologic features of lymphoid cell infiltrates in colorectal carcinoma (CRCs) that correlate with clinical parameters.

Assays, References, and Samples

The methods described herein include determining levels of selected immune-related genes, i.e., chemokines, cytotoxic cell genes, and/or dendritic cell genes. In some embodiments, all of the genes listed in the tables below are evaluated. In some embodiments, two, three, four, five, six, seven, eight, nine, ten, eleven, twelve, or more of the listed genes are evaluated. Although the terminology "genes" is used herein, in some embodiments, the methods include detecting levels of the proteins encoded by the listed genes. In some embodiments, the methods include detecting transcript (mRNA) levels.

Chemokines

Chemokines are secreted proteins involved in immunoregulatory and inflammatory processes. The chemokines used in the present methods are as follows:

| Chemokines | | | |
|---|---|---|---|
| Gene Symbol | Gene Name | GenBank Acc. No.: Nucleic Acid | GenBank Acc. No.: Protein |
| CCL2 | chemokine (C-C motif) ligand 2 | NM_002982.3 | NP_002973.1 |
| CCL3 | chemokine (C-C motif) ligand 3 | NM_002983.2 | NP_002974.1 |
| CCL4 | chemokine (C-C motif) ligand 4 | NM_002984.2 | NP_002975.1 |
| CCL5 | chemokine (C-C motif) ligand 5 | NM_002985.2 | NP_002976.2 |
| CCL8 | chemokine (C-C motif) ligand 8 | NM_005623.2 | NP_005614.2 |
| CCL18 | chemokine (C-C motif) ligand 18 (pulmonary and activation-regulated) | NM_002988.2 | NP_002979.1 |
| CCL19 | chemokine (C-C motif) ligand 19 | NM_006274.2 | NP_006265.1 |
| CCL21 | chemokine (C-C motif) ligand 21 | NM_002989.2 | NP_002980.1 |
| CXCL9 | chemokine (C-X-C motif) ligand 9 | NM_002416.1 | NP_002407.1 |
| CXCL10 | chemokine (C-X-C motif) ligand 10 | NM_001565.2 | NP_001556.2 |
| CXCL11 | chemokine (C-X-C motif) ligand 11 | NM_005409.4 | NP_005400.1 |
| CXCL13 | chemokine (C-X-C motif) ligand 13 | NM_006419.2 | NP_006410.1 |

Cytotoxic Cell Genes

The cytotoxic cell genes evaluated in the methods described herein are those expressed by cytotoxic cells involved in the immune response, e.g., lysosomal/proteolytic enzymes (cathepsins), granzymes, and FcgR2s.

| Cytotoxic Genes | | | |
|---|---|---|---|
| Gene Symbol | Gene Name | GenBank Acc. No.: Nucleic Acid | GenBank Acc. No.: Protein |
| CTSH | Cathepsin H | NM_004390.3 | NP_004381.2 |
| CTSC | Cathepsin C (Dipeptidyl peptidase 1) | NM_001814.4 | NP_001805.3 |
| CTSD | Cathepsin D | NM_001909.3 | NP_001900.1 |
| CTSE | Cathepsin E | NM_001910.2; NM_148964.1 | NP_001901.1; NP_683865.1 |
| CTSO | Cathepsin O | NM_001334.2 | NP_001325.1 |
| CTSS | Cathepsin S | NM_004079.3 | NP_004070.3 |
| CTSZ | Cathepsin Z | NM_001336.3 | NP_001327.2 |
| GZMA | Granzyme A | NM_006144.3 | NP_006135.1 |
| GZMB | Granzyme B | NM_004131.4 | NP_004122.2 |
| GZM H | Granzyme H | NM_033423.3 | NP_219491.1 |
| GZMK | Granzyme K | NM_002104.2 | NP_002095.1 |
| FCGR2A | Fcgamma receptor (FcgammaR) type IIa | NM_001136219.1.; NM_021642.3 | NP_001129691.1; NP_067674.2 |
| FCGR2B | Fcgamma receptor (FcgammaR) type IIb | NM_001002273.2 NM_001002274.2 NM_001002275.2 NM_001190828.1 NM_004001.4. | NP_001002273.1 NP_001002274.1 NP_001002275.1 NP_001177757.1 NP_003992.3 |
| FCGR2C | Fcgamma receptor (FcgammaR) type IIc | NM_201563.4 | NP_963857.3 |

-continued

| Cytotoxic Genes | | | |
|---|---|---|---|
| Gene Symbol | Gene Name | GenBank Acc. No.: Nucleic Acid | GenBank Acc. No.: Protein |
| FCGR3A | Fcgamma receptor (FcgammaR) type IIIa | NM_000569.6<br>NM_001127592.1<br>NM_001127593.1<br>NM_001127595.1<br>NM_001127596.1. | NP_000560.5<br>NP_001121064.1<br>NP_001121065.1<br>NP_001121067.1<br>NP_001121068.1 |
| FCGR3B | Fcgamma receptor (FcgammaR) type IIIb | NM_000570.3 | NP_000561.3. |

Dendritic Cell Genes

Most of the dendritic cell genes evaluated in the methods described herein belong to the S100 family of proteins, and contain two EF-hand calcium-binding motifs. S100 proteins are involved in the regulation of a number of cellular processes such as cell cycle progression and differentiation. CD209 is a pathogen-recognition receptor expressed on the surface of immature dendritic cells; it is believed to be involved in initiation of the primary immune response.

genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman, *Microarrays Methods and Applications: Nuts & Bolts*, DNA Press, 2003), can be used to detect the presence and/or level of chemokine proteins as described herein.

In some embodiments, the methods include assaying levels of one or more control genes or proteins, and comparing the level of expression of the immune-related genes or proteins to the level of the control genes or proteins, to normalize the levels of the immune-related genes or proteins. Suitable endogenous control genes includes a gene whose expression level should not differ between samples, such as a housekeeping or maintenance gene, e.g., 18S ribosomal RNA; beta Actin; Glyceraldehyde-3-phosphate dehydrogenase; Phosphoglycerate kinase 1; Peptidylprolyl isomerase A (cyclophilin A); Ribosomal protein L13a; large Ribosomal protein P0; Beta-2-microglobulin; Tyrosine 3-monooxygenase/tryptophan 5-monooxygenase activation protein, zeta polypeptide; Succinate dehydrogenase; Transferrin receptor (p90, CD71); Aminolevulinate, delta-, synthase 1; Glucuronidase, beta; Hydroxymethyl-bilane synthase; Hypoxanthine phosphoribosyltransferase 1; TATA box binding protein; and/or Tubulin, beta polypeptide.

| Dendritic Cell Genes | | | |
|---|---|---|---|
| Gene Symbol | Gene Name | GenBank Acc. No.: Nucleic Acid | GenBank Acc. No.: Protein |
| S100PBP | S100P Binding Protein | NM_022753.2 | NP_073590.2 |
| S100A10 | S100 calcium-binding protein A10 | NM_002966.2 | NP_002957.1 |
| S100A6 | S100 calcium-binding protein A6 | NM_14624.3 | NP_055439.1 |
| S100A7L1 | S100 calcium-binding protein A7-like 1 | NM_176823.3 | NP_789793.1 |
| S100G | S100 calcium-binding protein G | NM_004057.2 | NP_004048.1 |
| S100A1 | S100 calcium-binding protein A1 | NM_006271.1 | NP_006262.1 |
| S100A7 | S100 calcium-binding protein A7 | NM_002963.3 | NP_002954.2 |
| S100A14 | S100 calcium-binding protein A14 | NM_020672.1 | NP_065723.1 |
| S100A16 | S100 calcium-binding protein A16 | NM_080388.1 | NP_525127.1 |
| S100A2 | S100 calcium-binding protein A2 | NM_005978.3. | NP_005969.1 |
| S100A11 | S100 calcium-binding protein A11 | NM_005620.1 | NP_005611.1 |
| S100P | S100 calcium-binding protein P | NM_005980.2 | NP_005971.1. |
| S100Z | S100 calcium-binding protein Z | NM_130772.3 | NP_570128.2 |
| S100A3 | S100 calcium-binding protein A3 | NM_002960.1 | NP_002951.1 |
| S100A13 | S100 calcium-binding protein A13 | NM_001024210.1<br>NM_001024211.1<br>NM_001024212.1<br>NM_001024213.1<br>NM_005979.2 | NP_001019381.1<br>NP_001019382.1<br>NP_001019383.1<br>NP_001019384.1<br>NP_005970.1 |
| S100A12 | S100 calcium-binding protein A12 | NM_005621.1 | NP_005612.1 |
| S100B | S100 calcium-binding protein B | NM_006272.2 | NP_006263.1 |
| S100A4 | S100 calcium-binding protein A4 | NM_002961.2;<br>NM_019554.2 | NP_002952.1;<br>NP_062427.1 |
| S100A9 | S100 calcium-binding protein A9 | NM_002965.3 | NP_002956.1 |
| S100A8 | S100 calcium-binding protein A8 | NM_002964.3 | NP_002955.2 |
| CD209 | CD209 antigen | NM_001144893.1<br>NM_001144894.1<br>NM_001144895.1<br>NM_001144896.1<br>NM_001144897.1<br>NM_021155.3 | NP_001138365.1<br>NP_001138366.1<br>NP_001138367.1<br>NP_001138368.1<br>NP_001138369.1<br>NP_066978.1 |

In some embodiments, the methods include assaying the presence or levels of immune-related mRNA or proteins in the sample. The presence and/or level of a protein can be evaluated using methods known in the art, e.g., using quantitative immunoassay methods. The presence and/or level of an mRNA can be evaluated using methods known in the art, e.g., Northern blotting or quantitative PCR methods, e.g., RT-PCR. In some embodiments, high throughput methods, e.g., protein or gene chips as are known in the art (see, e.g., Ch. 12, Genomics, in Griffiths et al., Eds. Modern Generally speaking, the methods described herein can be performed on cells from a tumor. The cells can be obtained by known methods, e.g., during a biopsy (such as a core needle biopsy), or during a surgical procedure to remove all or part of the tumor. The cells can be used fresh, frozen, fixed, and/or preserved, so long as the mRNA or protein that is to be assayed is maintained in a sufficiently intact state to allow accurate analysis.

In some embodiments of the methods described herein, the levels of the immune-related genes in the tumor sample can be compared individually to levels in a reference. The reference levels can represent levels in a subject who has a good prognosis, or a long predicted survival time (e.g., 2 years or more). Alternatively, reference levels can represent levels in a subject who has a poor prognosis, or a shorter predicted survival time (e.g., less than 2 years). In some embodiments, the reference levels represent a threshold, and a level in the tumor that is above the threshold reference level indicates that the subject has a good prognosis, or a long predicted survival time (e.g., 2 years or more), and levels below the threshold reference level indicates that the subject has a poor prognosis, or a shorter predicted survival time (e.g., less than 2 years).

In some embodiments, the reference levels can represent levels in a subject who has lymphoid like structures present in the tumor, or is predicted to respond to immunotherapy. Alternatively, reference levels can represent levels in a subject who lacks tumor lymphoid structures, or is predicted to have no or a poor response to immunotherapy. In some embodiments, the reference levels represent a threshold, and a level in the tumor that is above the threshold reference level indicates that the subject has tumor lymphoid structures, or is predicted to respond to immunotherapy, and levels below the threshold reference level indicates that the subject lacks lymphoid structures and is predicted to have no or poor response to immunotherapy. In subjects who are predicted to have tumor lymphoid structures, or who are predicted to respond to immunotherapy, the methods can further include administering an immunotherapy for those subjects, or selecting or recommending a treatment including an immunotherapy for those subjects.

In some embodiments of the methods described herein, values representing the levels of the immune-related genes can be summed to produce a "tumor immune-related gene score" that can be compared to a reference immune-related gene score, wherein a tumor immune-related gene score that is above the reference immune-related gene score indicates that the subject has a long predicted survival time (e.g., 2 years or more) or is predicted to have a positive response to immunotherapy, and an immune-related gene score below the reference score indicates that the subject has a shorter predicted survival time (e.g., less than 2 years), or is predicted to have no or a poor response to immunotherapy.

For example, in some embodiments, the expression levels of each of the evaluated genes can be assigned a value (e.g., a value that represents the expression level of the gene, e.g., normalized to an endogenous control gene as described herein). That value (optionally weighted to increase or decrease its effect on the final score) can be summed to produce an immune-related gene score. One of skill in the art could optimize such a method to determine an optimal algorithm for determining an immune-related gene score.

The methods described herein can include determining levels (or scores) for all of the 12 chemokines, 20 dendritic cell genes, and 16 cytotoxic cell genes; or for the 12 chemokines and 20 dendritic cell genes; or for the 20 dendritic cell genes, and 16 cytotoxic cell genes; or for the 12 chemokines, and 16 cytotoxic cell genes, or for any of the gene sets alone. In some embodiments all of the genes in each set are evaluated, but in some embodiments a subset of one or all of the sets is evaluated.

One of skill in the art will appreciate that references can be determined using known epidemiological and statistical methods, e.g., by determining an immune-related gene score, or immune-related gene protein or mRNA levels, in tumors from an appropriate cohort of subjects, e.g., subjects with the same type of cancer as the test subject and a known prognosis (e.g., good or poor) or predicted survival time (e.g., less than 2 years, or 2 years or more).

In some embodiments, the methods can be used to monitor the efficacy of a treatment, e.g., an immunotherapy, e.g., methods comprising administering to the subject therapies that promote anti-cancer immunity, including administering one or more of: dendritic cells or peptides with adjuvant, DNA-based vaccines, cytokines (e.g., IL-2), cyclophosphamide, anti-interleukin-2R immunotoxins, and/or antibodies such as anti-CD137, anti-PD1, or anti-CTLA-4; see, e.g., Kruger et al., "Immune based therapies in cancer," Histol Histopathol. 2007 June; 22(6):687-96; Eggermont et al., "Anti-CTLA-4 antibody adjuvant therapy in melanoma," Semin Oncol. 2010 October; 37(5):455-9; Klinke D J 2nd, "A multiscale systems perspective on cancer, immunotherapy, and Interleukin-12," Mol Cancer. 2010 Sep. 15; 9:242; Alexandrescu et al., "Immunotherapy for melanoma: current status and perspectives," J Immunother. 2010 July-August; 33(6):570-90; Moschella et al., "Combination strategies for enhancing the efficacy of immunotherapy in cancer patients," Ann N Y Acad Sci. 2010 April; 1194:169-78; Ganesan and Bakhshi, "Systemic therapy for melanoma," Natl Med J India. 2010 January-February; 23(1):21-7; Golovina and Vonderheide, "Regulatory T cells: overcoming suppression of T-cell immunity," Cancer J. 2010 July-August; 16(4):342-7. In some embodiments, the methods include administering a composition comprising tumor-pulsed dendritic cells, e.g., as described in WO2009/114547 and references cited therein. The methods include determining levels of the immune-related genes in a sample, then administering one or more doses of the treatment, then determining levels of the immune-related genes to determine whether the treatment has increase immune infiltration of the tumor. An increase in immune-related gene levels (or immune-related gene score, if calculated) indicates that the treatment was effective.

EXAMPLES

The invention is further described in the following examples, which do not limit the scope of the invention described in the claims.

Statistical analysis for the following examples was performed as follows. On the figure legends, the term "significance" denoted p-value by Fisher exact test. Throughout the paper, for each gene, a single probe set with highest standard deviation across all samples, was selected among multiple probesets available on the array that mapped to the same gene symbol. Significance of linkages of gene profiles to patient survival was analyzed statistically by both ANOVA and Wilcoxon Rank-Sum tests.

Example 1. Immune Gene Profiling

Several metagenes—tightly correlated sets of genes biologically related to inflammation and immune response—were identified. Metagene analysis was performed on samples from the Moffitt Cancer Center (MCC) CRC500 tumor bank and CRCs were sorted by low versus high scores.

Selection of human tissues was performed as follows. The MCC CRC500 gene profiling database was interrogated for the presence of genes biologically related to inflammation and immune response. The 11 CRCs with the highest expression of these genes (2 of the CRCs, denoted T2157A1 and T2157A3, are separate samples obtained from the same patient) were selected and compared with the 10 CRCs with the lowest or absent expression of the same genes. The histologic slides corresponding to these cases, and prepared from the mirror-image of the portion of tumor submitted for the mRNA microarray analysis, were retrieved from the MCC Anatomic Pathology Division's repository. All of the specimens were preserved in 10% buffered formalin prior to embedding in paraffin. The slides were reviewed to assess the presence of microscopically evident host immune response. The final pathology report for each case was also reviewed and the pathologic data were collected.

The tumors were staged according to both Dukes and TNM systems. All tumors occurred in the absence of genetic cancer syndromes such as human non-polyposis colon cancer syndrome (HNPCC), familial adenomatous polyposis syndrome (FAP), among others; also cancers arising in the background of ulcerative colitis or Crohn's disease were excluded from the study. Linked, annotated clinical follow-up data (e.g., survival) and treatments received were also available in the database.

mRNA microarray analysis was performed as follows. Twelve normal colorectal mucosa samples, 9 normal liver samples, and 326 colorectal adenocarcinoma tumor specimens (19 annotated as metastasis, 265 as primary, and 42 as unknown) from human patients were arrayed on Affymetrix HG-U133+ GENECHIP microarrays (quartz chips for analysis of DNA; denoted MCC CRC500). For the current study, this existing MCC CRC500 database was interrogated and the data were processed using RMA normalization algorithm as implemented in Affymetrix POWER TOOLS software package (APT; which are a set of cross-platform command line programs that implement algorithms for analyzing and working with Affymetrix GENECHIP arrays) using default settings. Obtained probe set intensities were then converted to log10. Probes were selected for heatmaps by starting with all gene symbols from a given family and then reducing to probes that showed a desired correlation pattern.

Three hundred and twenty six "gene chipped" CRCs were evaluated from this tumor bank. The chip contained 20,155 unique genes. About 50 separate metagene groupings were derived. Among them a metagene (Metagene #1) with overwhelming enrichment for immune- and inflammation-related genes was identified. It is also the largest metagene in terms of number of genes (comprising 320 unique immune gene symbols). FIG. 1A shows the 21 of 326 CRCs selected by the 11 highest and 10 lowest values of the mean score of metagene #1.

Example 2. Pathologic and Clinical Findings

The patients with 21 CRCs selected by the 11 highest and 10 lowest values of the mean score of metagene #1 had a median age of 69 years (range, 51-83). Thirteen were male and seven were female. Most of the primary CRCs were moderately differentiated (n=16); of these 8 were metagene #1 "high" and 8 were metagene #1 "low". Three tumors were well differentiated; of these one was metagene #1 "high" and two were metagene #1 "low". One CRC was poorly differentiated and it was metagene #1 "high". Thus, there was no definable correlation between CRCs selected by metagene #1 and their grade of differentiation.

Figure 1B:
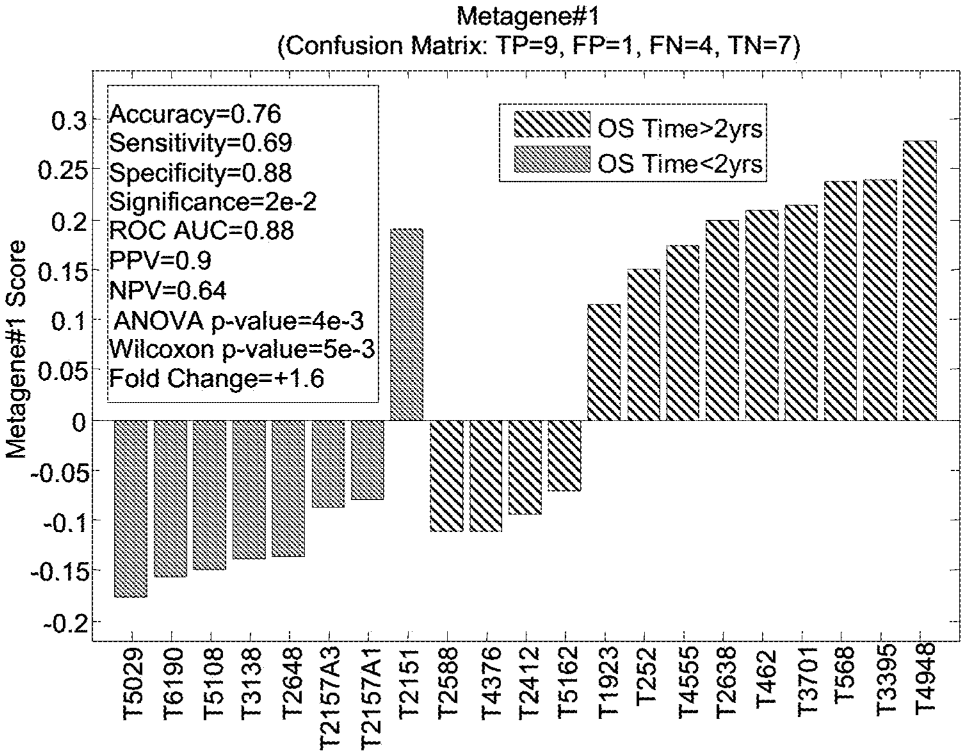
FIG. 1B is a bar graph illustrating of the relationship between patient overall survival and the immune response as quantified by the score of metagene #1 on selected CRCs with known status of ectopic lymph node-like structures confirmed by immunohistochemistry. The barplot of CRCs without lymphoid structures and CRCs with lymphoid structures segregated into two groups: those with overall survival time less than 2 years (shown on the left), and those with overall survival time greater than 2 years (shown on the right). Score for metagene #1 is plotted on the Y-axis.

The relationship between overall survival of the patients and the immune response as quantified by the score of metagene #1 for the 21 selected CRCs was also examined. FIG. 1B shows the bar plot of these two groups of metagene #1 selected CRCs: those with overall survival time less than 2 years (shown on the left), and those with overall survival time greater than 2 years (shown on the right). Score for metagene #1 is plotted on the Y-axis. As can be seen, there was a significant trend of increased overall survival (>2 years) of patients with CRCs with the highest values of the mean score of metagene #1.

Example 3. Histopathologic and Immunohistochemical Findings

Immunohistochemistry and analysis were performed as follows. The tissues were stained using the avidin-biotin-complex method with retrieval under high pH. Prediluted, monoclonal antibodies (mAb) to CD3 (rabbit mAb, Ventana Medical Systems, Inc., Tucson, Ariz.), CD20 (mouse mAb, Ventana), CD79a (mouse mAb, Ventana), Ki-67 (rabbit mAb, Ventana), and CD21 (mouse mAb, Novocastra Laboratories Ltd., Newcastle upon Tyne, UK) were used for the analysis of lymphoid infiltrates. The slides were de-paraffinized by heating at 56° C. for 30 minutes and by three washes, five minutes each, with xylene. Tissues were rehydrated by a series of five-minute washes in 100%, 95%, and distilled water. After blocking with universal blocking serum (Ventana) for 30 minutes, the samples were incubated with each primary mAb at 37° C. for 32 minutes. The samples were then incubated with biotin-labeled secondary mAb and streptavidin-horseradish peroxidase for 30 minutes each. The slides were developed with 3,3'-diaminobenzidine tetrahydrochloride substrate (Ventana) and counterstained with hematoxylin and bluing (Ventana). The tissue samples were dehydrated and coverslipped. Appropriate cell conditioning (following the Ventana recommendations) was used for antigen retrieval for all antibodies. A negative control was included of non immune mouse sera and omitting the primary antibody during the primary antibody incubation step. The positive controls were selected following the Ventana recommendations for CD3, CD20, CD79a, and Ki-67, and the Novocastra recommendations for CD21.

The mAb stained tissue slides were blinded and examined by two independent pathologists simultaneously. In case of discrepancy a consensus was reached by the re-valuation of the slides. The positivity of the stains was calculated semi-quantitatively by estimating the percent of nuclear positivity in the lymphoid cells.

Microscopically, all 10 of the lowest metagene #1-scored CRCs revealed a minimally dispersed or absent lymphocytic peritumoral host response, and low to no appreciable expression for lymphocytic markers (FIGS. 2A, B). Conversely, all 11 of the highest metagene #1-scored CRCs, revealed a marked peritumoral lymphocytic host response organized, remarkably, as ectopic lymph node-like structures by hematoxylin and eosin staining (FIG. 2C) and by immunohistochemistry (FIGS. 2D-I), particularly at the invasive edge of the tumors. Of note, there was no statistically significant difference between the presence of ectopic lymph node-like structures and gender (p>0.5), tumor grade (p>0.5), tumor site location (p>0.5; Table 2), and tumor stage (p>0.5; Table 2).

Ectopic lymph node-like structures were observed intratumorally as well, occasionally accompanied by a lightly diffuse pattern of lymphocytes within the tumor parenchyma. The lymphoid structures were found to contain follicles. The majority of the $CD3^+$ T cells were located in parafollicular cortex-like zones (FIGS. 2D, H, I); scattered $CD3^+$ T cells were occasionally seen within these tumors as well. $CD20^+$ B cells were present almost exclusively within the follicular structures (FIGS. 2E, F). In every case, $CD79a^+$ B cell precursors were identified within the lymphoid follicles (FIG. 2G). $CD21^+$ dendritic cells were present within the follicular germinal centers, establishing the true follicular nature of the lymphoid aggregates (FIG. 2J). The Ki-67 expression was found only in the highest metagene #1-scored CRC cases, suggesting that these germinal centers are in different stage of maturation. Lymphocytic proliferation was found to contain both B and T lymphocytes, which suggests newly formed and/or activated ectopic lymph node-like structures. Together, these findings support the hypothesis that these follicles represent secondary and/or tertiary ectopic lymph node-like structures.

Example 4. Identification of a Chemokine Gene Signature 326 colorectal tumors and 12 genes comprising metagene #1 were sorted by the metagene score (mean of probesets that map to a given 12-gene, gene set). Again, the 11 samples with the highest metagene score (shown on the previous Figures) are shown at the top, and 10 samples with the lowest metagene score (shown on the previous Figures) are shown at the bottom. Table 1 shows the hierarchical clustering of 326 CRC tumors and the selected 12 chemokines (i.e., CCL2, CCL3, CCL4, CCL5, CCL8, CCL18, CCL19, CCL21, CXCL9, CXCL10, CXCL11, and CXCL13) that were most correlated with the metagene #1 score. For each chemokine, the label provides gene symbol, numerical order on the corresponding probeset when processed with APT package, as well as probeset identification. Collectively, these data demonstrate that the chemokines, because of their potent, biologic attraction of immune cell subtypes track strongly with the formation or presence of ectopic lymph node-like structures in CRC tumor masses.

TABLE 1

Chemokine Gene Expression in Human Colon Tumors: A 12 Gene Signature Predicts Presence of Ectopic Lymph Nodes
* Colon500, Chemokine Correlation to Metagene#1

| probe# | probeset | symbol† | rho | p-value |
|---|---|---|---|---|
| 65 | 1405_i_at | CCL5 | 83% | 0E+00 |
| 17867 | 204655_at | CCL5 | 83% | 0E+00 |
| 52045 | 1555759_a_at | CCL5 | 81% | 0E+00 |
| 17288 | 205242_at | CXCL13 | 72% | 0E+00 |
| 18402 | 204103_at | CCL4 | 72% | 0E+00 |
| 18665 | 203915_at | CXCL9 | 72% | 0E+00 |
| 18007 | 204533_at | CXCL10 | 66% | 7E−42 |
| 12512 | 210072_at | CCL19 | 61% | 4E−34 |
| 235 | 32128_at | CCL18 | 58% | 2E−30 |
| 8658 | 214038_at | CCL8 | 58% | 1E−30 |
| 12636 | 209924_at | CCL18 | 58% | 8E−31 |
| 6122 | 216598_s_at | CCL2 | 57% | 4E−30 |
| 17425 | 205114_s_at | CCL3 | 56% | 2E−28 |
| 11482 | 211122_s_at | CXCL11 | 55% | 1E−27 |
| 12419 | 210163_at | CXCL11 | 55% | 1E−27 |
| 17905 | 204606_at | CCL21 | 53% | 5E−25 |

Table 1. * Hierarchical clustering of 326 CRCs and selected
†12 chemokines (CCL2, CCL3, CCL4, CCL5, CCL8, CCL18, CCL19, CCL21, CXCL9, CXCL10, CXCL11, CXCL13) that are most correlated with metagene # score. Tumors are sorted by the metagene score, chemokines are clustered using Pearson correlation distance metric and Ward linkage. For each chemokine, the label provides gene symbol, numerical order on the corresponding probeset when processed with APT package, as well as probeset id. Rho, Pearson correlation coefficient.

Figure 3A:
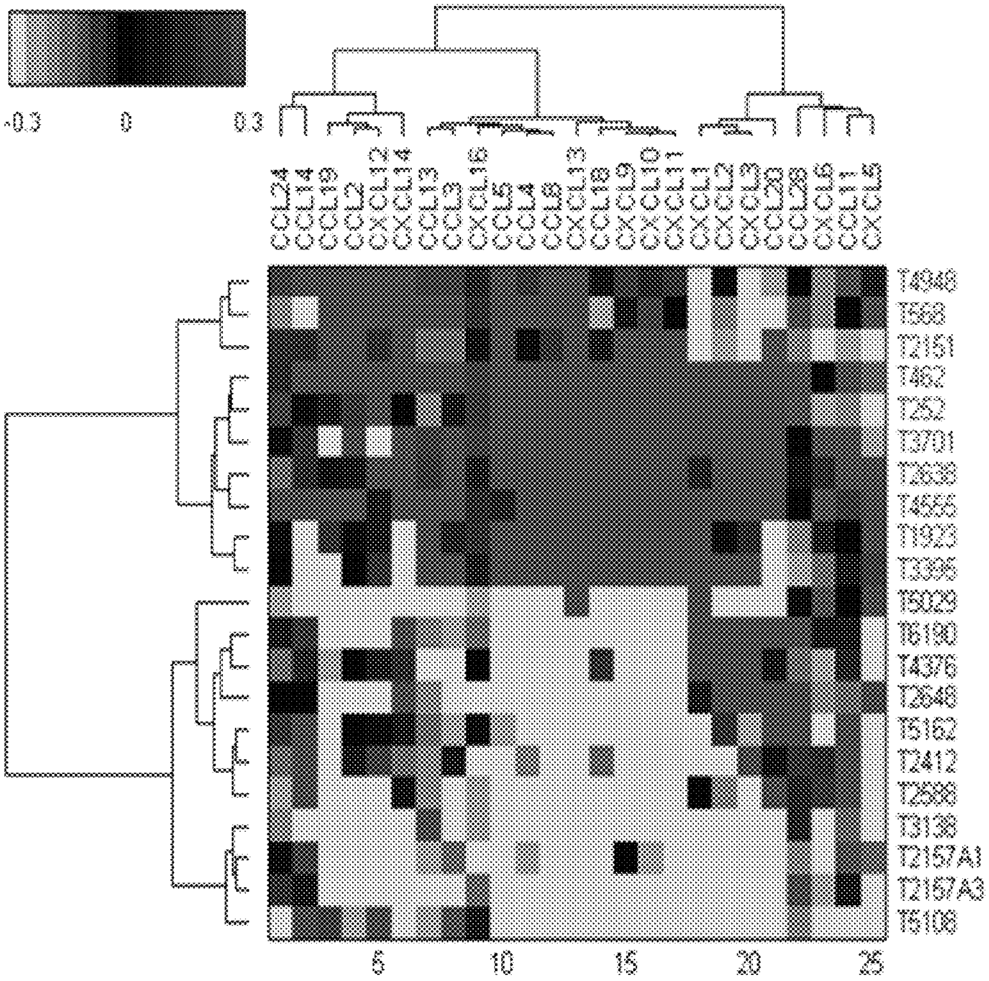
FIGS. 3A-B show that chemokines are upregulated in tumors with lymphocyte involvement. Hierarchical clustering of tumors with and without lymphoid structures done on selected set of known chemokines. For each gene, a single representative probe set with the highest dynamic range across all profiled samples was picked up from all probe sets that mapped to a given gene symbol. Genes are clustered using Pearson correlation distance metric, tumors are clustered using Euclidean distance metric. Ward linkage was applied in both cases, for clustering tumors and genes.
Figure 3B:
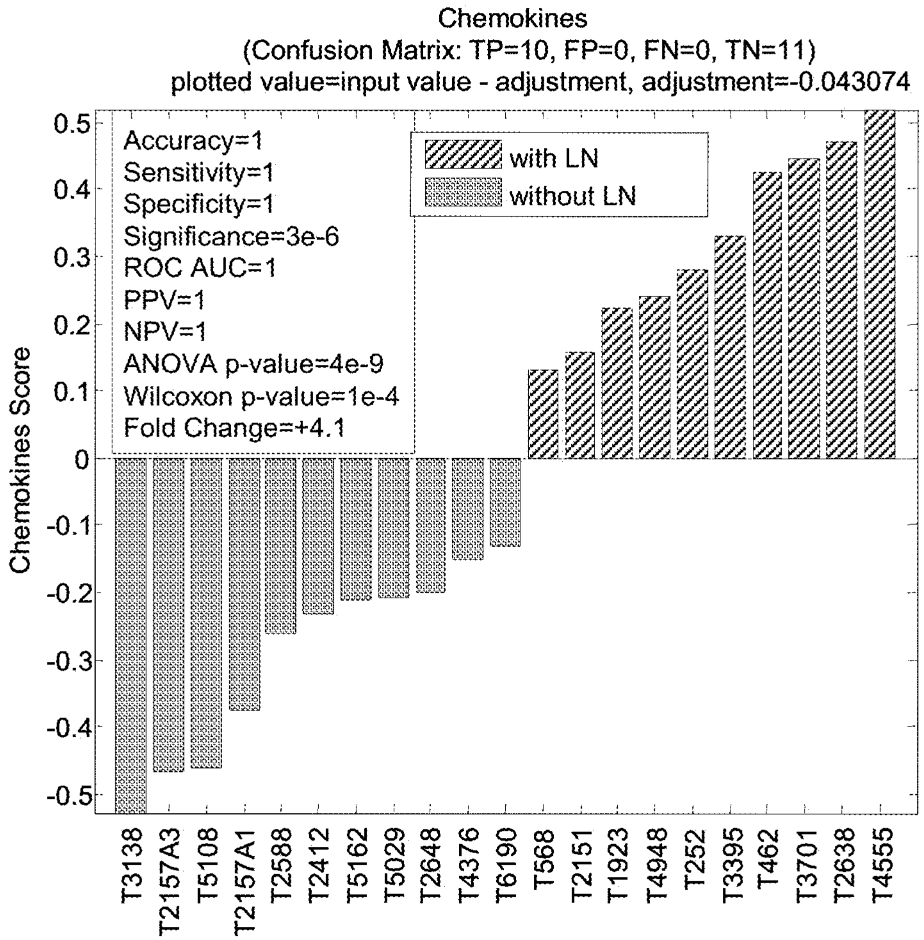

There was a strong correlation of association between the chemokine gene profile and the presence of ectopic lymph node-like structures in CRCs (See FIG. 3A). Hierarchical clustering of tumors with and without lymphoid structures was performed on a selected set of known chemokine genes (shown in FIG. 3B). Strong correspondence exists between score mean cutoffs for metagene #1 and the chemokine gene set. For each gene, a single representative probe set with the highest dynamic range across all profiled samples was picked from all probe sets that mapped to a given gene symbol. Genes are clustered using Pearson correlation distance metric; tumors are sorted by gene scores (shown in in FIG. 3B).

Example 5. Molecular Signatures and Clinical Parameters

Table 2 shows that metagene #1 and the 12-chemokine gene signature that identify the presence of ectopic lymph node-like structures in CRCs are independent of tumor staging (TNM and Dukes), tumor site location, and treatment received (e.g., surgery alone, surgery plus chemotherapy with or without external beam radiation).

TABLE 2

Molecular Signatures that Identify the Presence of Ectopic Lymph Node Structures are Independent of Tumor Site Location, Stage and Patient Treatment

| Signatures* | Tumor† | Ectopic Lymph Nodes | Tumor Site | Dukes/ TNM Stage | Treatment |
|---|---|---|---|---|---|
| + | T2151 | + | Rectum | D/IVA | 5FU |
| + | T4555 | + | Left | B/IIA | None |
| + | T252 | + | Right | C/IIIC | 5FU + radiation |
| + | T2638 | + | Rectum | C/IIIB | 5FU/Irinotecan |
| + | T4948 | + | Sigmoid | C/IIIB | 5FU + radiation |
| + | T1923 | + | Left | B/IIA | 5FU |
| + | T462 | + | Rectum | B/IIA | None |
| + | T568 | + | Left | NA‡ | 5FU/mitomycin/ Irinotecan + radiation |
| + | T3701 | + | Right | C/IIIB | 5FU |
| + | T3395 | + | Sigmoid | B/IIB | None |
| − | T5108 | − | Right | NA‡ | 5FU |
| − | T2648 | − | Rectum | −/0 | None |
| − | T5029 | − | Sigmoid | C/IIIB | NA |
| − | T3138 | − | Left | NA‡ | 5FU/Irinotecan |
| − | T6190 | − | Sigmoid | D/IVA | 5FU/Irinotecan/ Erbitux/Irinotecan |
| − | T2588 | − | Left | B/IIC | 5FU/Irinotecan/5−FUDR + mitomycin/ Irinotecan + radiation |
| − | T2157A1/ A3 | − | Right | D/IVA | None |
| − | T4376 | − | Left | B/IIC | 5FU/Irinotecan |
| − | T5162 | − | Left | B/IIC | 5FU + radiation |
| − | T2412 | − | Left | C/IIIB | 5FU/Irinotecan/Erbitux |

Table 2. Molecular Signatures are Independent of Tumor Stage and Patient Treatment.
*Metagene #1 and 12-chemokine signature.
†CRCs that have the 10 highest and 10 lowest metagene #1 and 12-chemokine signature scores.
‡Not available.

Figure 4A:
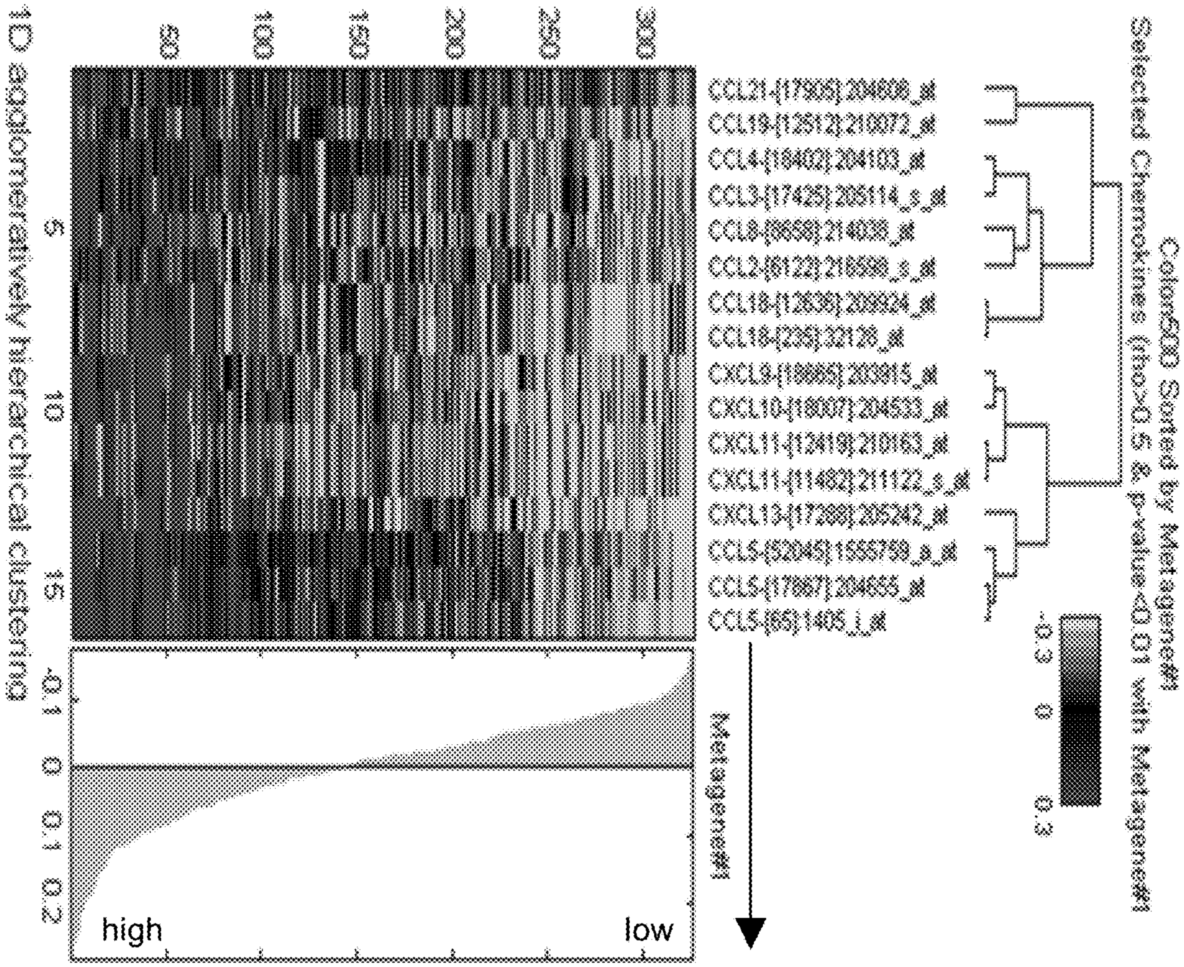
FIG. 4A is a heat map showing 12 chemokines that correlate with metagene #1. The heatmap of 326 colorectal tumors and 12 genes comprising metagene #1 sorted by the metagene score (mean of probesets that map to a given 12-gene gene set). The 11 samples with the highest metagene score are at the top of the figure, and 10 samples with the lowest metagene score are at the bottom of this figure.
Figure 4B:
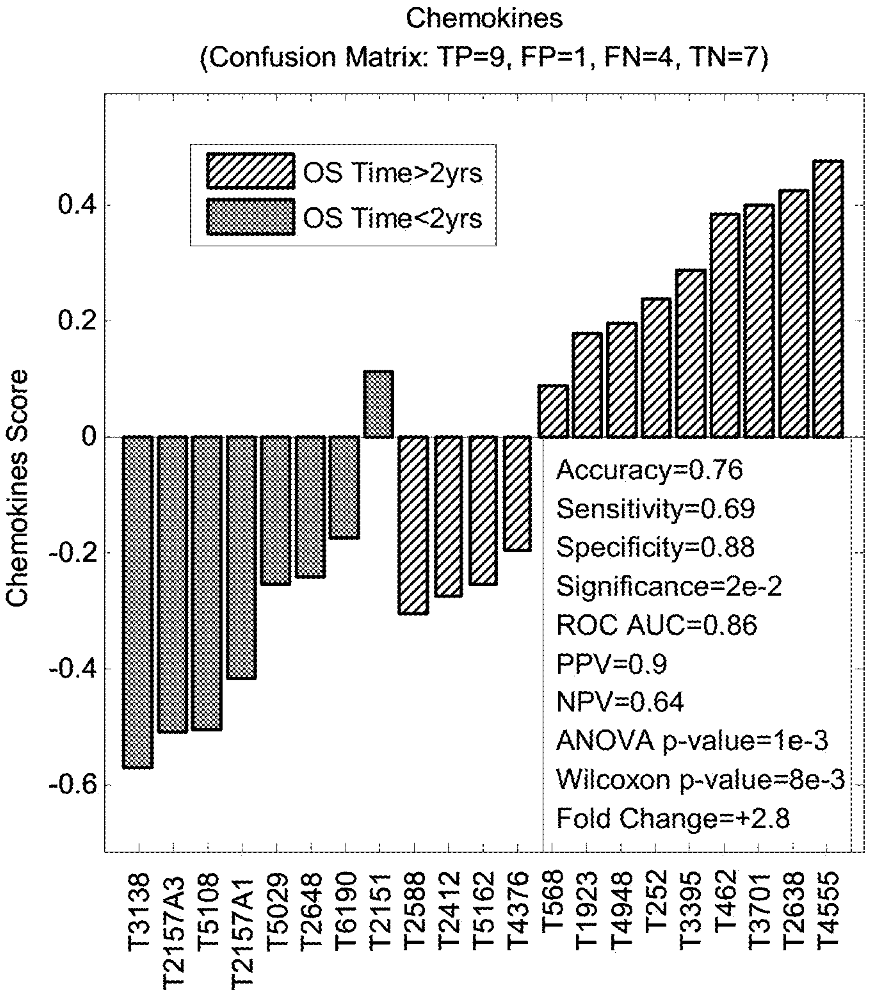
FIG. 4B is a bar graph illustrating the relationship between patient overall survival and the immune response as quantified by the score of chemokine genes on selected CRCs with known status of ectopic lymph node-like structures confirmed by immunohistochemistry. The barplot of CRCs without lymphoid structures and CRCs with lymphoid structures segregated into two groups: those with overall survival time less than 2 years (shown on the left), and those with overall survival time greater than 2 years (shown on the right). Scores for the chemokine genes are plotted on the Y-axis.

The relationship between overall survival of the patients and metagene #1 and the 12-chemokine gene signature was also examined for the 21 selected CRCs. FIG. 4B shows the bar plots of these groups of signature-selected CRCs: those with overall survival time less than 2 years (shown on the left), and those with overall survival time greater than 2 years (shown on the right). Score for genes is plotted on the Y-axis. As can be seen, there was a significant trend of increased overall survival (>2 years) of patients with CRCs with the highest values of the mean score of the 12-chemokine gene signature.

Example 6. Identification of T Cell Activation-Related Gene Signatures

Figure 5A:
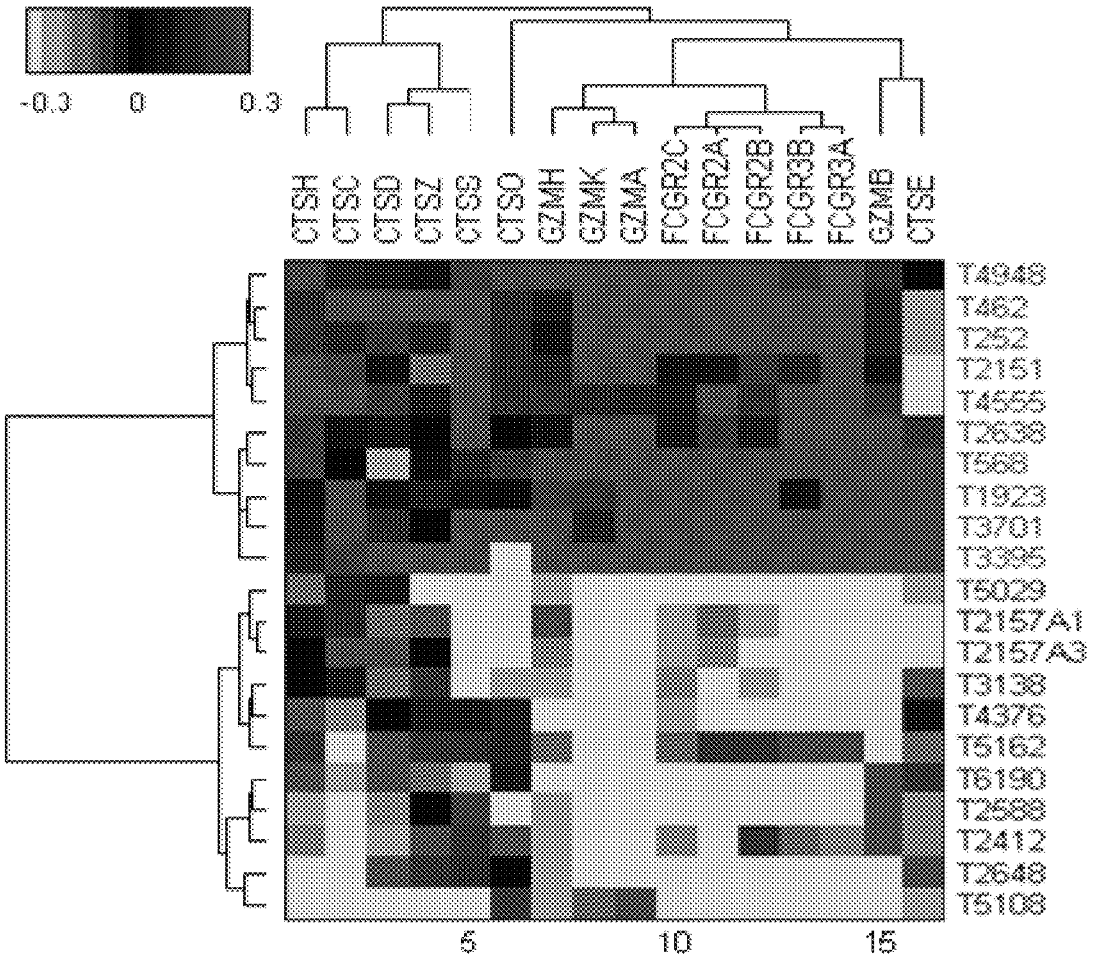
FIGS. 5A-B show that cytotoxic genes are upregulated in tumors with ectopic lymph node-like structures. Hierarchical clustering of tumors with and without lymphoid structures were performed on a selected set of known cytotoxic genes. For each gene, a single representative probe set with the highest dynamic range across all profiled samples was picked up from all probe sets that mapped to a given gene symbol. Genes are clustered using Pearson correlation distance metric; tumors are clustered using Euclidean distance metric. Ward linkage was applied in both cases, for clustering tumors and genes.
Figure 5B:
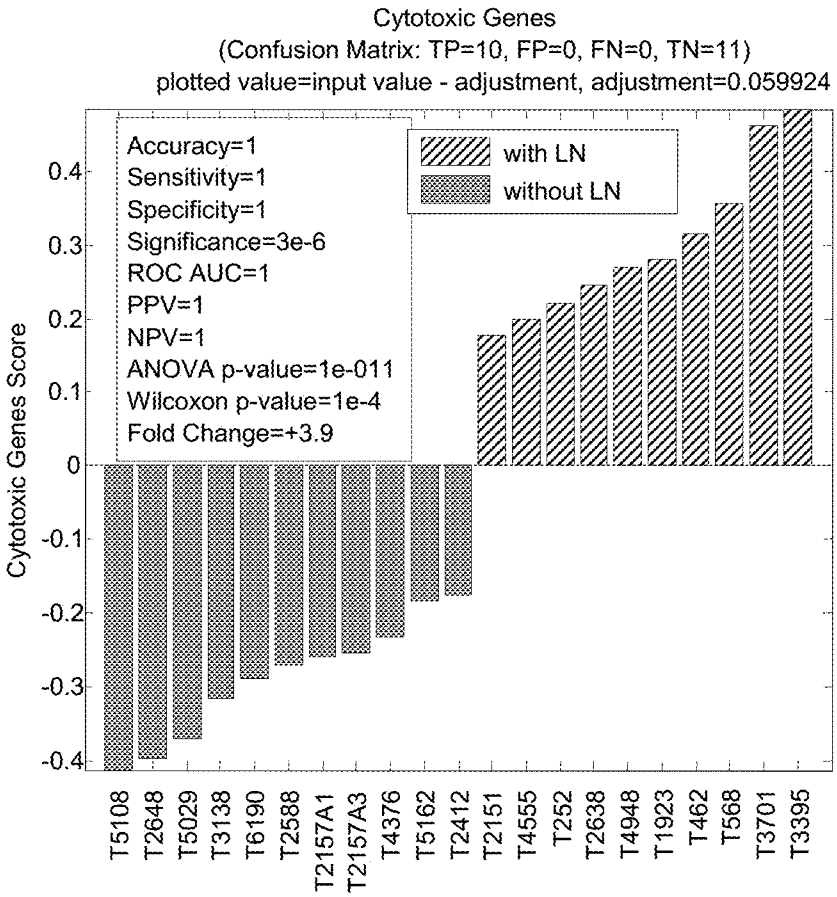
Figure 6A:
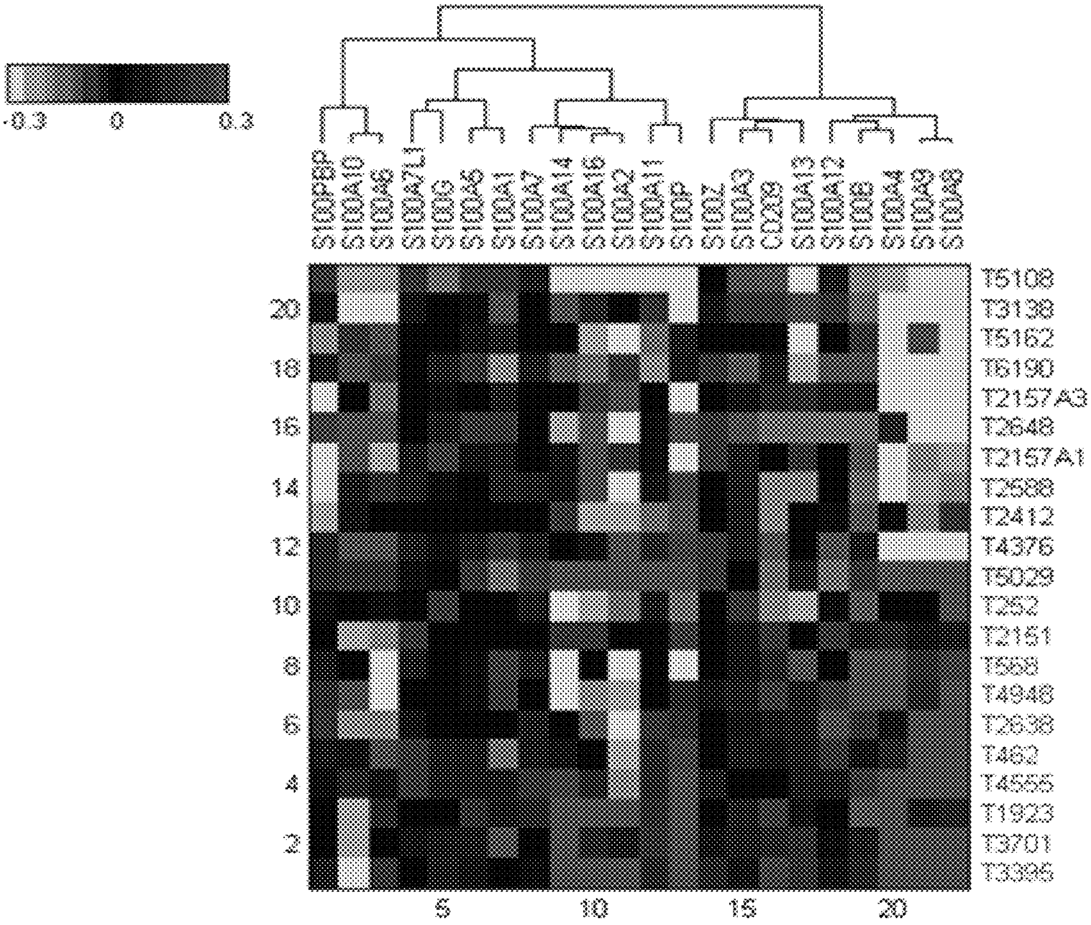
FIGS. 6A-B show that dendritic cell marker genes are upregulated in CRCs with ectopic lymph node involvement. Hierarchical clustering of tumors with and without lymphoid structures was done on a selected set of known dendritic cell marker genes. For each gene, a single representative probe set with the highest dynamic range across all profiled samples was picked up from all probe sets that mapped to a given gene symbol. Genes are clustered using Pearson correlation distance metric, tumors are sorted by the dendritic genes score (shown in 6B) computed as the mean value for each tumor across all genes shown on the figure. Ward linkage was applied for clustering genes.
Figure 6B:
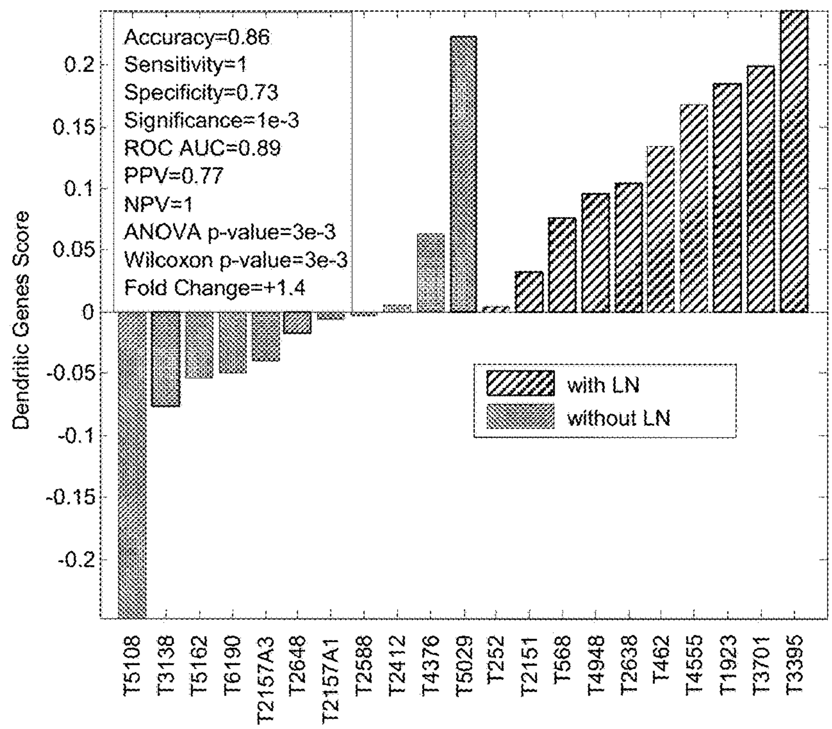

The heatmaps of FIGS. 5A and 6A show strong correlations of association between cytotoxic cell (lysosomal/proteolytic enzymes, granzymes, FcgR2s) and dendritic cell (S100 family, CD209) gene profiles, respectively, and the presence of ectopic lymph node-like structures in CRCs. Hierarchical clustering of tumors with and without ectopic lymph node-like structures were then performed on a selected set of known cytotoxic- and dendritic cell-related genes (shown in FIGS. 5B and 6B). Strong correspondence exists between score mean cutoffs for metagene #1 and cytotoxic and dendritic cell-related gene sets. For each gene, a single representative probe set with the highest dynamic range across all profiled samples was picked up from all probe sets that mapped to a given gene symbol. Genes are clustered using Pearson correlation distance metric; tumors are sorted by the genes score (shown in FIGS. 5 and 6) and are computed as the mean value for each tumor across all genes shown. Collectively, the cytotoxic and dendritic cell genes reflect an important immune cell composition of ectopic lymph node-like structures in CRC.

Figure 7A:
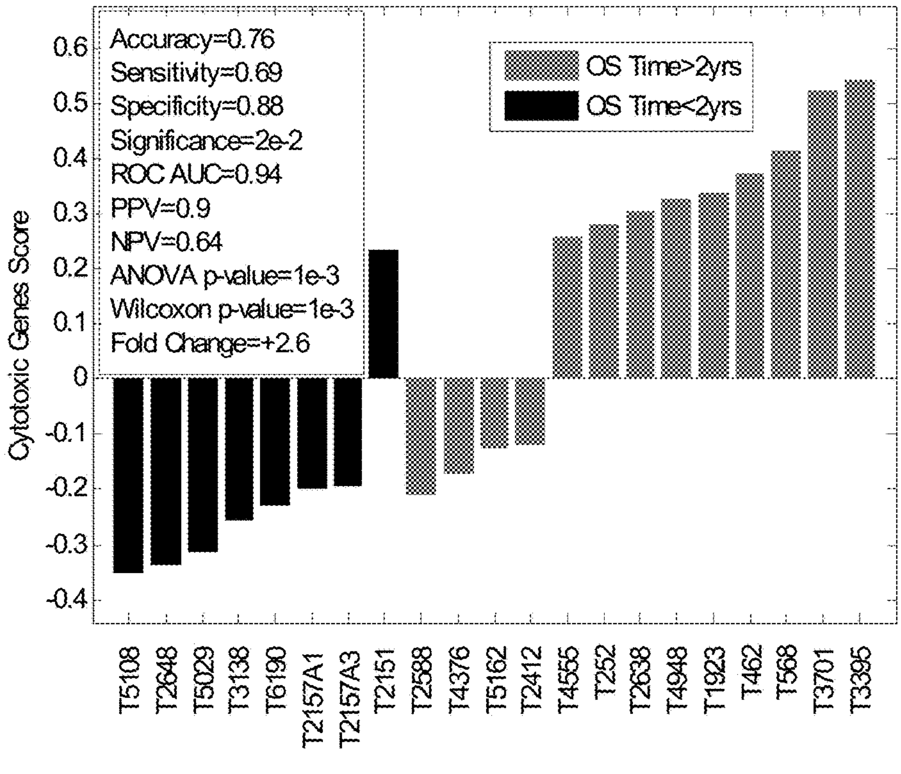
FIGS. 7A-B are bar graphs illustrating the relationship between patient overall survival and the immune response as quantified by the score of cytotoxic cell—(7A) and dendritic cell—( 7B) related genes on selected CRCs with known status of ectopic lymph node-like structures confirmed by immunohistochemistry. The barplot of CRCs without lymphoid structures and CRCs with lymphoid structures segregated into two groups: those with overall survival time less than 2 years (shown on the left), and those with overall survival time greater than 2 years (shown on the right). Scores for cytotoxic cell- and dendritic cell-related genes are plotted on the Y-axis.
Figure 7B:
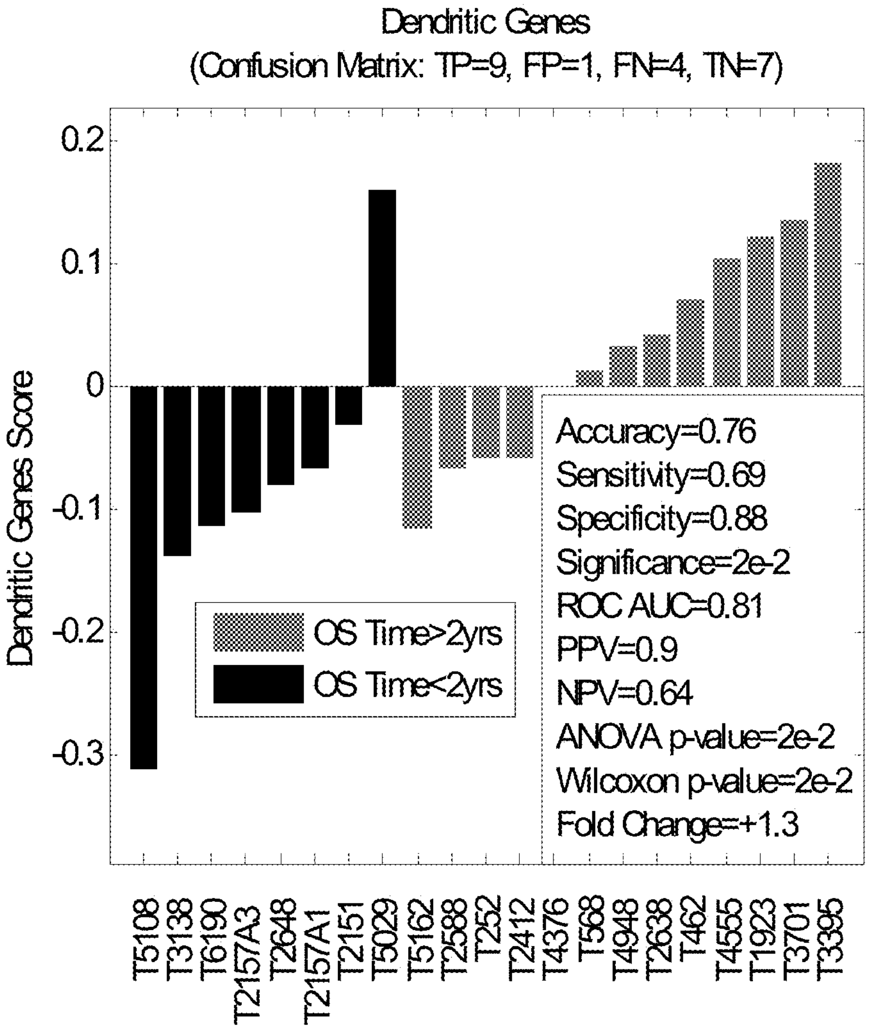

FIGS. 7A-B show the bar plots of these groups of signature-selected CRCs: those with overall survival time less than 2 years (shown on the left), and those with overall survival time greater than 2 years (shown on the right). Score for genes is plotted on the Y-axis. As can be seen, there was a significant trend of increased overall survival (>2 years) of patients with CRCs with the highest values of the mean score of the cytotoxic and dendritic cell gene signatures.

REFERENCES

1. Jemal A, Siegel R, Ward E, Hao Y, Xu J, Murray T, Thun M J: Cancer Statistics. CA Cancer J Clin 2008, 58: 71-96
2. Coronella J A, Spier C, Welch M, Trevor K T, Stopeck A T, Villar H, Hersh E M: Antigen-driven oligoclonal expansion of tumor-infiltrating B cells in infiltrating ductal carcinoma of the breast. J Immunol 2002, 169: 1829-1836
3. Coronella-Wood J A, Hersh E M: Naturally occurring B-cell responses to breast cancer. Review. Cancer Immunol Immunother 2003, 52:715-738
4. Bell D, Chomarat P, Broyles D, Netto G, Harb G M, Lebecque S, Valladeau J, Davoust J, Palucka K A, Banchereau J: In breast carcinoma tissue, immature dendritic cells reside within the tumor, whereas mature dendritic cells are located in peritumoral areas. J Exp Med 1999, 190: 1417-1426
5. Aspord C, Pedroza-Gonzalez A, Gallegos M, Tindle S, Burton E C, Su D, Marches F, Banchereau J, Palucka A K: Breast cancer instructs dendritic cells to prime interleukin 13-secreting CD4+ T cells that facilitate tumor development. J Exp Med 2007, 204: 1037-1047
6. Kurabayashi A, Furihata M, Matsumoto M, Hayashi H, Ohtsuki Y: Distribution of tumor-infiltrating dendritic cells in human non-small cell lung carcinoma in relation to apoptosis. Pathol Int 2004, 54: 302-310
7. Dieu-Nosjean M C, Antoine M, Danel C, Heudes D, Wislez M, Poulot V, Rabbe N, Laurans L, Tartour E, de Chaisemartin L, Lebecque S, Fridman W H, Cadranel J: Long-term survival for patients with non-small-cell lung cancer with intratumoral lymphoid structures. J Clin Oncol 2008, 26: 4410-4417
8. Eisenthal A, Polyvkin N, Bramante-Schreiber L, Misonznik F, Hassner A, Lifschitz-Mercer B: Expression of dendritic cells in ovarian tumors correlates with clinical outcome in patients with ovarian cancer. Hum Pathol 2001, 32: 803-807
9. Curiel T J, Coukos G, Zou L, Alvarez X, Cheng P, Mottram P, Evdemon-Hogan M, Conejo-Garcia J R, Zhang L, Burow M, Zhu Y, Wei S, Kryczek I, Daniel B, Gordon A, Myers L, Lackner A, Disis M L, Knutson K L, Chen L, Zou W: Specific recruitment of regulatory T cells in ovarian carcinoma fosters immune privilege and predicts reduced survival. Nat Med 2004, 10: 942-949
10. Singh P, Coskun Z Z, Goode C, Dean A, Thompson-Snipes L, Darlington G: Lymphoid neogenesis and immune infiltration in aged liver. Hepatology 2008, 47:1680-1690
11. Carragher D M, Rangel-Moreno J, Randall T D: Ectopic lymphoid tissues and local immunity. Semin Immunol 2008, 20: 26-42
12. Chiba T, Ohtani H, Mizoi T, Naito Y, Sato E, Nagura H, Ohuchi A, Ohuchi K, Shiiba K, Kurokawa Y, Satomi S: Intraepithelial CD8+ T-cell-count becomes a prognostic factor after a longer follow up period in human colorectal carcinoma: possible association with suppression of micrometastasis. Br J Cancer 2004, 91: 1711-1717
13. Nagorsen D, Keilholz U, Rivoltini L, Schmittel A, Letsch A, Asemissen A M, Berger G, Buhr H J, Thiel E, Scheibenbogen C: Natural T-cell response against MHC class I epitopes of epithelial cell adhesion molecule, her-2/neu, and carcinoembryonic antigen in patients with colorectal cancer. Cancer Res 2000, 60: 4850-4854
14. Ropponen K M, Eskelinen M J, Lipponen P K, Alhava E, Veli-Matti K: Prognostic value of tumour-infiltrating lymphocytes (TILs) in colorectal cancer. J Pathol 1997, 182: 318-324
15. Chaves P, Cruz C, Lage P, Claro I, Cravo M, Leitao C N, Soares J: Immunohistochemical detection of mismatch repair gene proteins as a useful tool for the identification of colorectal carcinoma with the mutator phenotype. J Pathol 2000, 191: 355-360
16. Kakar S, Aksoy S, Burgart L J, Smyrk T C: Muscinous carcinoma of the colon: correlation of loss of mismatch repair enzymes with clinicopathologis features and survival. Modern Pathol 2004, 17: 696-700
17. Tougeron D, Fauquembergue, E, Rouquette A, Le Pessot F, et al. Tumor-infiltrating lymphocytes in colorectal cancers with microsatellite instability are correlated with the number and spectrum of frameshift mutations. Modern Pathol 2009, 22: 1186-1195
18. Luscieti P, Hubschmid T, Cottier H, Hess M W, Sobin L H: Human lymph node morphology as a function of age and site. J Clin Pathol 1980, 33: 454-461
19. Zeid N A, Muller H K: S100 positive dendritic cells in human lung tumors associated with cell differentiation and enhanced survival. Pathology 1993, 25: 338-343
20. Nagorsen D, Voigt S, Berg E, Stein H, Thiel E, Loddenkemper C: Tumor-infiltrating macrophages and dendritic cells in human colorectal cancer: Relation to local regulatory T cells, systemic T-cell response against tumor-associated antigens and survival. J Transl Med 2007, 5: 62
21. Michael-Robinson J M, Biemer-Hütmann A, Purdie D M, Walsh M D, Simms L A, Biden K G, Young J P, Leggett B A, Jass J R, Radford-Smith G L: Tumour infiltrating lymphocytes and apoptosis are independent features in colorectal cancer stratified according to microsatellite instability status. Gut 2001, 48: 360-366
22. Coppola D, Mulé J J: Ectopic lymph nodes within human solid tumors. J Clin Oncol 2008, 26: 4369-4370
23. Timmer T C, Baltus B, Vondenhoff M, Huizinga T W, Tak P P, Verweij C L, Mebius R E, van der Pouw Kraan T C: Inflammation and ectopic lymphoid structures in rheumatoid arthritis synovial tissues dissected by genomics technology: Identification of the interleukin-7 signaling pathway in tissues with lymphoid neogenesis. Arthritis Rheum 2007, 56: 2492-2502
24. Olszewski W L: De novo lymph node formation in chronic inflammation of the human leg. Ann NY Acad Sci 2002, 979: 166-177
25. Marinkovic T, Garin A, Yokota Y, Fu Y X, Ruddle N H, Furtado G C, Lira S A: Interaction of mature CD3+CD4+ T cells with dendritic cells triggers the development of tertiary lymphoid structures in the thyroid. J Clin Invest 2006, 116: 2622-2632
26. Kim M Y, Gaspal F M, Wiggett H E, McConnell F M, Gulbranson-Judge A, Raykundalia C, Walker L S, Goodall M D, Lane P J: CD4+CD3− accessory cells costimulate primed CD4 T cellsthrough OX40 and CD30 at sites where T cells collaborate with B cells. Immunity 2003, 18: 643-654
27. van de Pavert S A, Olivier B J, Goverse G, Vondenhoff M F, Greuter M, Beke P, Kusser K, Höpken U E, Lipp M, Niederreither K, Blomhoff R, Sitnik K, Agace W W, Randall T D, de Jonge W J, Mebius R E: Chemokine CXCL13 is essential for lymph node initiation and is induced by retinoic acid and neuronal stimulation. Nat Immunol 2009, 10: 1193-1199
28. Kirk C J, Hartigan-O'Connor D, Mulé J J: The dynamics of the T-cell antitumor response: Chemokine-secreting dendritic cells can prime tumor-reactive T cells extranodally. Cancer Res 2001, 61: 8794-8802
29. Dubinett S M, Lee J M, Sharma S, Mulé J J: Chemokines: Can Effector Cells be Re-directed to the Site of Tumor? In: V. DeVita, T. Lawrence and S.A. Rosberg (eds). The Cancer Journal: Principles and Practice of Oncology. 2010 (in press)
30. Hoelzinger D B, Smith S E, Mirza N, Dominguez A L, Manrique S Z, Lustgarten J: Blockade of CCL1 inhibits T regulatory cell suppressive function enhancing tumor immunity without affecting T effector responses. J Immunol 2010, 184: 6833-6842
31. Mira E, León B, Barber D F, Jiménez-Baranda S, Goya I, Almonacid L, Márquez G, Zaballos A, Martínez-A C, Stein J V, Ardavín C, Mañes S: Statins induce regulatory T cell recruitment via a CCL1 dependent pathway. J Immunol 2008, 181: 3524-3534
32. Yamazaki T, Yang X O, Chung Y, Fukunaga A, Nurieva R, Pappu B, Martin-Orozco N, Kang H S, Ma L, Panopoulos A D, Craig S, Watowich S S, Jetten A M, Tian Q, Dong C: CCR6 regulates the migration of inflammatory and regulatory T cells. J Immunol 2008, 181: 8391-8401
33. Curiel T J, Coukos G, Zou L, Alvarez X, Cheng P, Mottram P, Evdemon-Hogan M, Conejo-Garcia J R, Zhang L, Burow M, Zhu Y, Wei S, Kryczek I, Daniel B, Gordon A, Myers L, Lackner A, Disis M L, Knutson K L, Chen L, Zou W: Specific recruitment of regulatory T cells in ovarian carcinoma fosters immune privilege and predicts reduced survival. Nature Med 2004, 10: 942-949
34. Toulza F, Nosaka K, Tanaka Y, Schioppa T, Balkwill F, Taylor G P, Bangham C R: Human T-lymphotropic virus type 1-induced CC chemokine ligand 22 maintains a high frequency of functional FoxP3+ regulatory T cells. J Immunol 2010, 185: 183-189
35. Harlin H, Meng Y, Peterson A C, Zha Y, Tretiakova M, Slingluff C, McKee M, Gajewski T F: Chemokine expression in melanoma metastases associated with CD8+ T-cell recruitment. Cancer Res 2009, 69: 3077-3085.
36. Manzo A, Paoletti S, Carulli M, Blades M C, Barone F, Yanni G, Fitzgerald O, Bresnihan B, Caporali R, Montecucco C, Uguccioni M, Pitzalis C: Systematic microanatomical analysis of CXCL13 and CCL21 in situ production and progressive lymphoid organization in rheumatoid synovitis. Eur J Immunol 2005, 35: 1347-1359
37. Galon J, Costes A, Sanchez-Cabo F, Kirilovsky A, Mlecnik B, Lagorce-Pagès C, Tosolini M, Camus M, Berger A, Wind P, Zinzindohoué F, Bruneval P, Cugnenc P H, Trajanoski Z, Fridman W H, Pagès F: Type, density, and location of immune cells within human colorectal tumors predict clinical outcome. Science 2006, 313: 1960-1964
38. Bogunovic D, O'Neill D W, Belitskaya-Levy I, Vacic V, Yu Y L, Adams S, Darvishian F, Berman R, Shapiro R, Pavlick A C, Lonardi S, Zavadil J, Osman I, Bhardwaj N: Immune profile and mitotic index of metastatic melanoma lesions enhance clinical staging in predicting patient survival. Proc Natl Acad Sci USA 2009, 106: 20429-20434
39. GeurtsvanKessel C H, Willart M A, Bergen I M, van Rijt L S, Muskens F, Elewaut D, Osterhaus A D, Hendriks R, Rimmelzwaan G F, Lambrecht B N: Dendritic cells are crucial for maintenance of tertiary lymphoid structures in the lung of influenza virus-infected mice. J Exp Med 2009, 206: 2339-2349
40. Tsunoda T, Yamakawa M, Takahashi T: Differential expression of Ca(2+)-binding proteins on follicular dendritic cells in non-neoplastic and neoplastic lymphoid follicles. Am J Pathol 1999, 155: 805-814
41. Yeatman T, Mulé J J, Dalton W S, Sullivan D: On the eve of personalized medicine in oncology. Cancer Res 2008, 68:7250-7252

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of establishing a chemokine gene signature for a solid tumor in a subject, the method consisting of:

obtaining cells from the tumor;

determining expression levels of a set of genes, wherein the set of genes consists of 12 genes consisting of chemokine (C-C motif) ligand 2 (CCL2), CCL3, CCL4, CCL5, CCL8, chemokine (C-C motif) ligand 18

(pulmonary and activation-regulated) (CCL18), CCL19, CCL21, chemokine (C-X-C motif) ligand 9 (CXCL9), CXCL10, CXCL11, and CXCL13 in the tumor cells;

comparing the expression levels of the set of genes in the tumor to reference gene expression levels, and calculating a gene score for the tumor by summing the expression levels of the set of 12 evaluated genes.

2. The method of claim 1, wherein determining gene expression levels comprises determining protein levels or mRNA levels.

3. The method of claim 2, wherein determining mRNA levels comprises using reverse transcription polymerase chain reaction or a microarray.

4. The method of claim 1, wherein the subject is a human.

5. The method of claim 1, wherein the tumor is non-small-cell lung cancer, melanoma, renal cell cancer, breast cancer, colorectal cancer, head and neck cancer, or ovarian cancer.

6. A method of establishing a chemokine gene signature for a solid tumor in a subject, the method consisting of:

obtaining cells from the tumor;

determining expression levels of a set of genes, wherein the set of genes consists of 12 genes consisting of chemokine (C-C motif) ligand 2 (CCL2), CCL3, CCL4, CCL5, CCL8, chemokine (C-C motif) ligand 18 (pulmonary and activation-regulated) (CCL18), CCL19, CCL21, chemokine (C-X-C motif) ligand 9 (CXCL9), CXCL10, CXCL11, and CXCL13 in the tumor cells; and comparing the expression levels of the set of genes in the tumor to reference gene expression levels.

7. The method of claim 6, wherein determining gene expression levels comprises determining protein levels or mRNA levels.

8. The method of claim 7, wherein determining mRNA levels comprises using reverse transcription polymerase chain reaction or a microarray.

9. The method of claim 6, wherein the subject is a human.

10. The method of claim 6, wherein the tumor is non-small-cell lung cancer, melanoma, renal cell cancer, breast cancer, colorectal cancer, head and neck cancer, or ovarian cancer.

* * * * *